United States Patent [19]
Li et al.

[11] Patent Number: 5,916,144
[45] Date of Patent: *Jun. 29, 1999

[54] SYSTEM FOR INTRODUCING A FLUID INTO THE UTERUS OF AN ANIMAL

[75] Inventors: Jiewen Li, Houston, Tex.; August Rieke, Bland, Mo.; Billy N. Day, Auxvasse, Mo.; Randall S. Prather, Rocheport, Mo.

[73] Assignee: The Curators of the University of Missouri, Columbia, Mo.

[ * ] Notice: This patent is subject to a terminal disclaimer.

[21] Appl. No.: 08/964,833

[22] Filed: Nov. 5, 1997

Related U.S. Application Data

[63] Continuation-in-part of application No. 08/438,174, May 9, 1995, Pat. No. 5,558,636, and a continuation-in-part of application No. 08/438,162, May 9, 1995, Pat. No. 5,656,010.

[51] Int. Cl.$^6$ .............................. A61B 17/43; A61D 7/00
[52] U.S. Cl. .............................. 600/34; 604/49; 604/280; 128/898
[58] Field of Search ..................................... 600/562, 564, 600/565, 567, 563, 34, 35, 33, 591; 606/119, 126, 127, 125, 159; 604/170, 53, 55, 96, 280, 49, 54, 171, 165, 169, 264; 128/898

[56] References Cited

U.S. PATENT DOCUMENTS

| | | |
|---|---|---|
| 1,150,214 | 8/1915 | London ................................. 600/166 |
| 3,811,443 | 5/1974 | Dickson, III et al. .................... 600/35 |
| 4,192,294 | 3/1980 | Vasilevsky et al. ..................... 606/128 |
| 4,318,414 | 3/1982 | Schuster et al. . |
| 4,453,936 | 6/1984 | Cassou . |
| 4,642,094 | 2/1987 | North, Jr. et al. . |
| 4,832,681 | 5/1989 | Lenck . |
| 4,865,589 | 9/1989 | Simmet et al. . |
| 5,084,004 | 1/1992 | Ranoux ................................... 600/34 |
| 5,147,315 | 9/1992 | Weber . |
| 5,464,409 | 11/1995 | Mohajer . |
| 5,472,419 | 12/1995 | Bacich . |

FOREIGN PATENT DOCUMENTS

| | | | |
|---|---|---|---|
| 71538 | 2/1983 | European Pat. Off. ................ | 600/34 |
| 1525336 | 5/1968 | France .................................... | 600/35 |
| 6-154254 | 6/1994 | Japan ..................................... | 600/34 |
| 2263642 | 8/1993 | United Kingdom .................... | 600/34 |

OTHER PUBLICATIONS

"Reproduction Resources Artificial Breeding Equipment and Veterinary Supplies", no date, pp. 1A, 1B, 1–17, 17A (admitted prior art).

Reichenbach, H.D. et al., "Piglets Born After Transcervical Transfer of Embryos Into Recipient Gilts", *Veterinary Record*, 4 pages. (1993).

Galvin, J.M. et al., "A Procedure for Successful Nonsurgical Embryo Transfer in Swine", pp. 1280–1289, (1994).

Polge, C. et al. "Pregnancy Following Non–surgical Egg Transfer in Pigs", published in *The Veterinary Record*, Apr. 15, 1968.

Sims, M.M. et al., "Nonsurgical Embryo Transfer in Swine", published in the *Journal of Animal Science*, vol. 65, Supplement 1, p. 386 (1987).

Hazeleger, W. et al., "Non–surgical Transfer of Porcine Blastocyst" published in the *Theriogenology, an International Journal of Animal Reproduction*, vol. 43, No. 1, p. 232 (1995).

*Primary Examiner*—Richard J. Apley
*Assistant Examiner*—Justine R. Yu
*Attorney, Agent, or Firm*—Senniger, Powers, Leavitt & Roedel

[57] ABSTRACT

This invention relates to a system for penetrating the uterus of an animal during a non-surgical procudure, the uterus having a cervix leading to a uterus body. The system comprises a probe having a long tubular body with a central longitudinal axis, open forward and rearward ends, and a probing member projecting forward and laterally outward beyond the forward end of the probe body. The probe is inserted, forward end first, inside the cervix of said animal, and the probe body is manipulated to gently maneuver the probing member in a forward direction through the cervix to a position in which the probing member and the forward open end of the probe body are adjacent the body of the uterus.

11 Claims, 15 Drawing Sheets

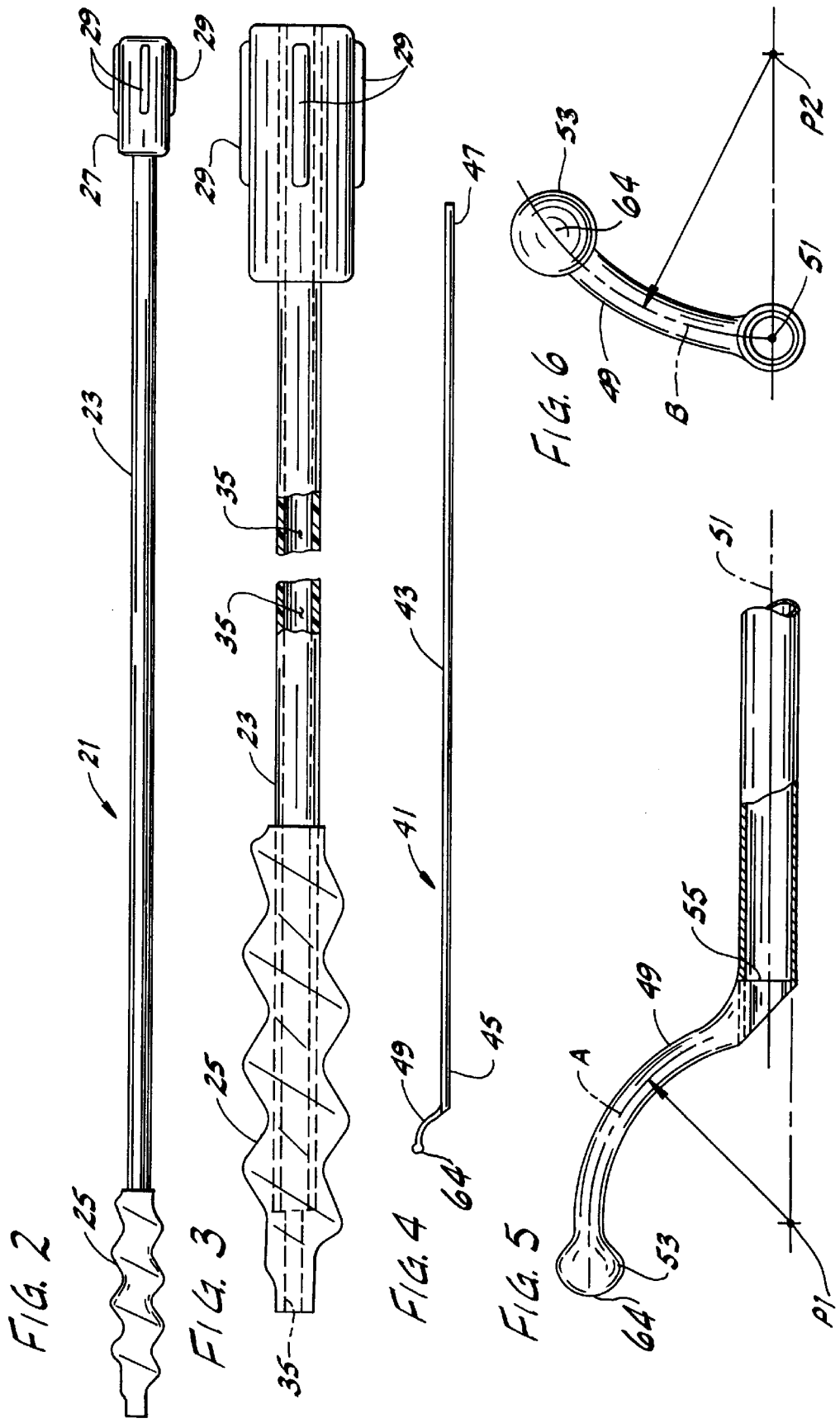

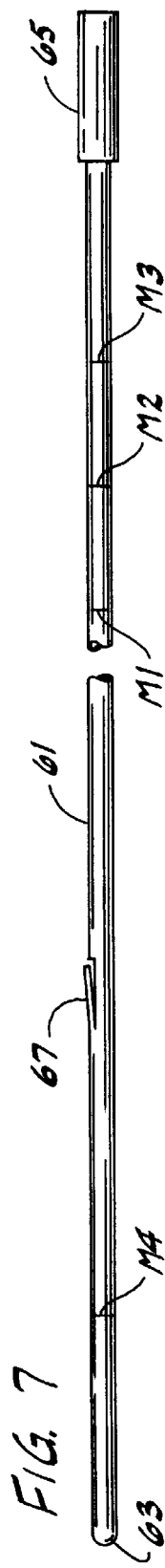
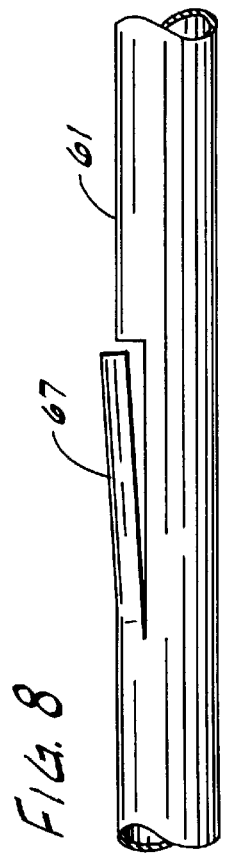
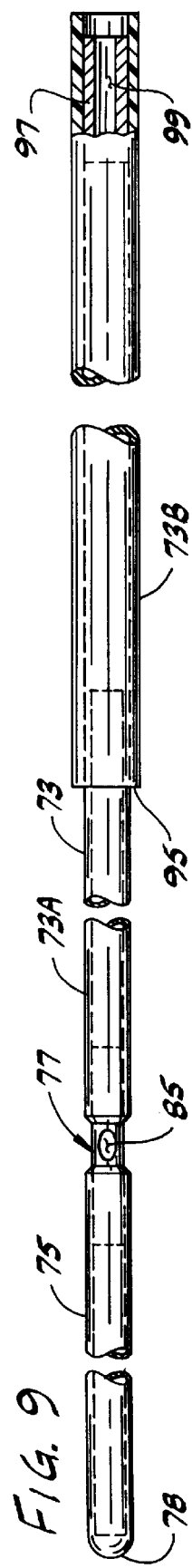
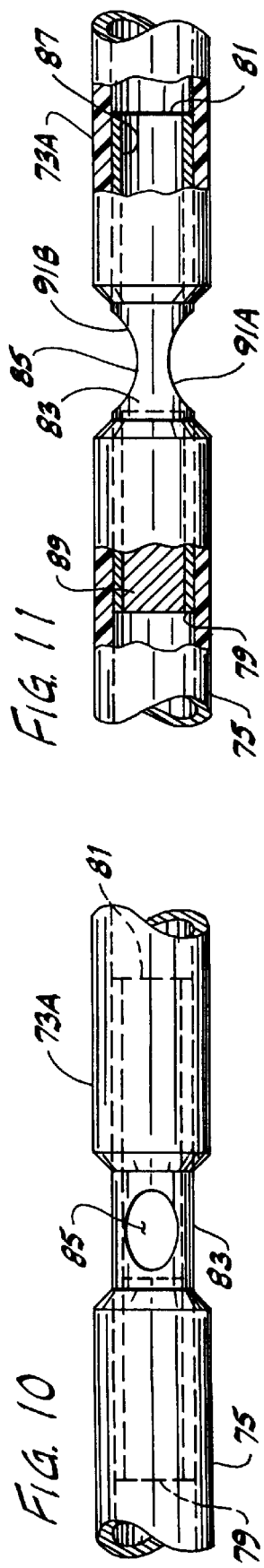
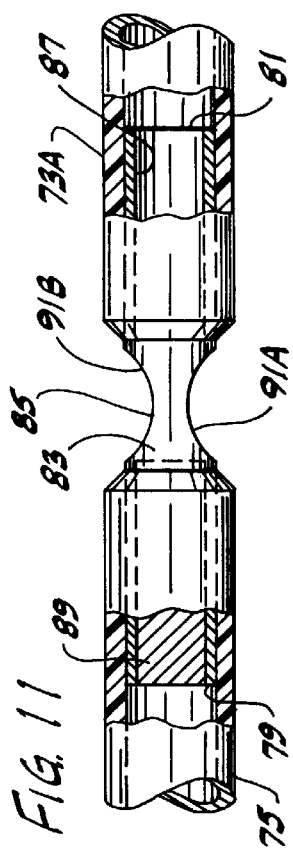

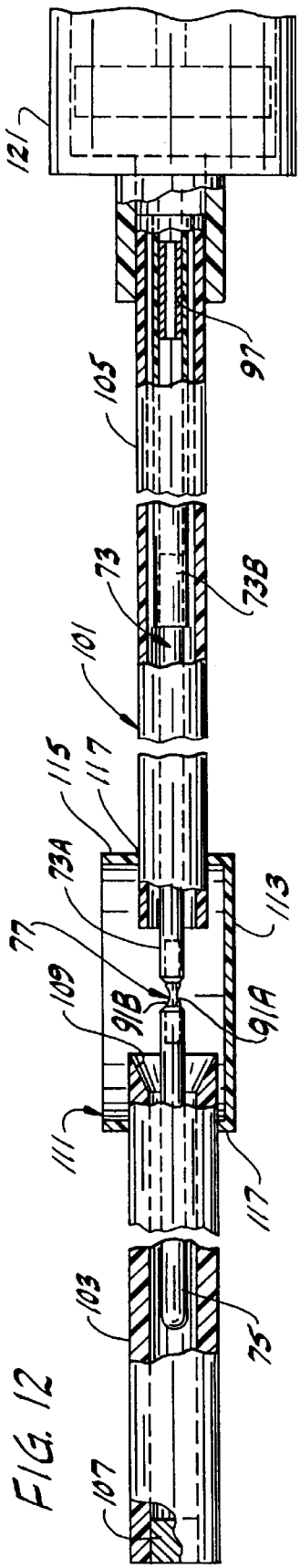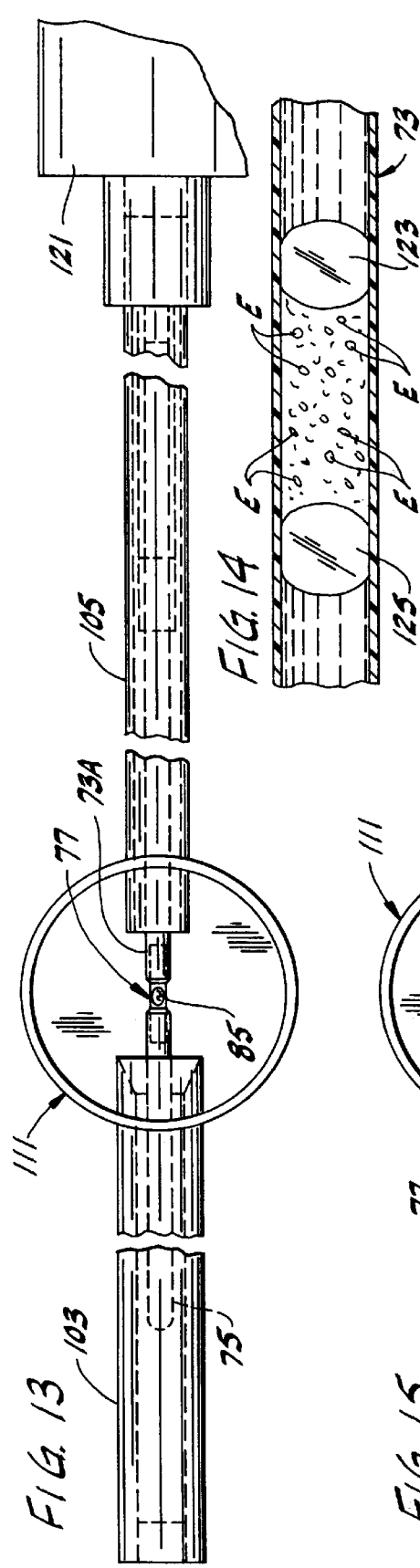

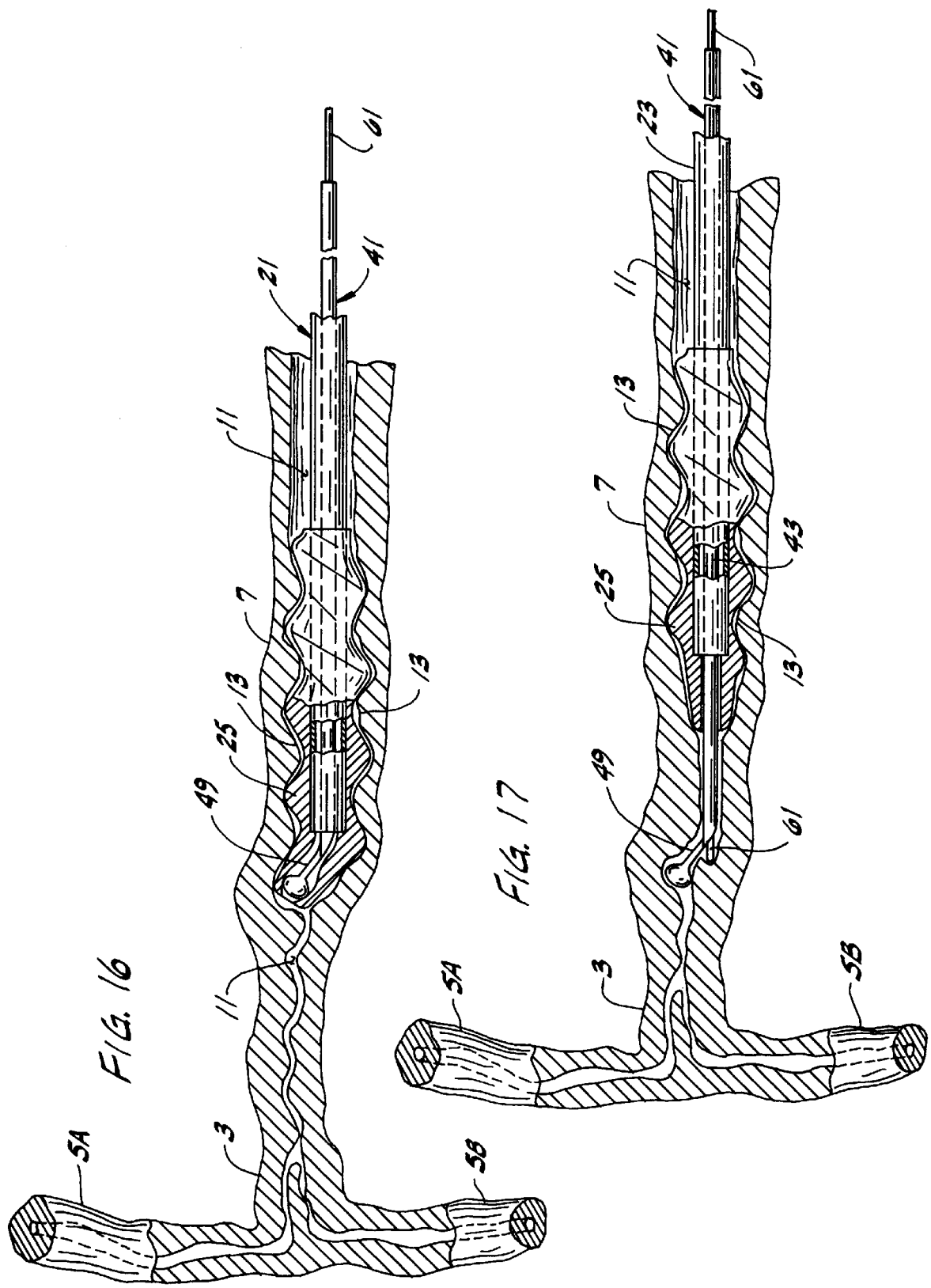

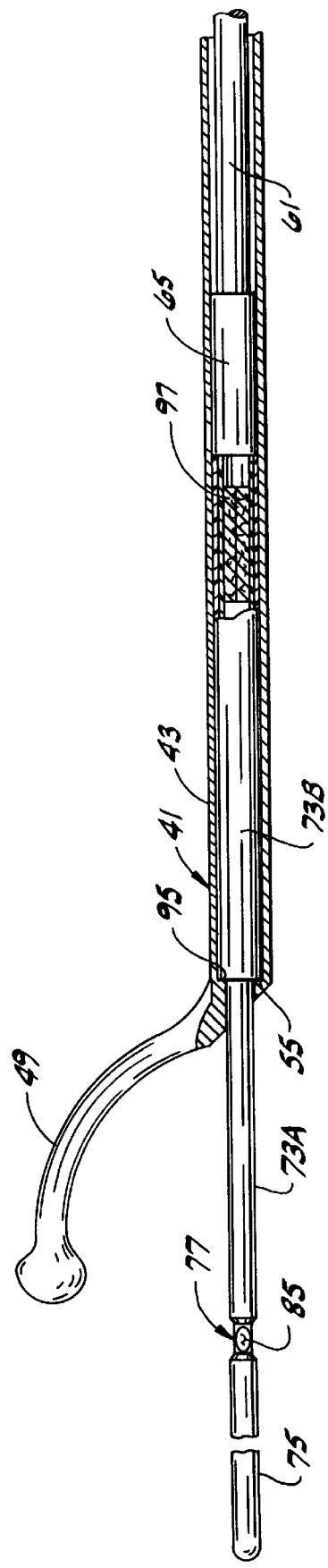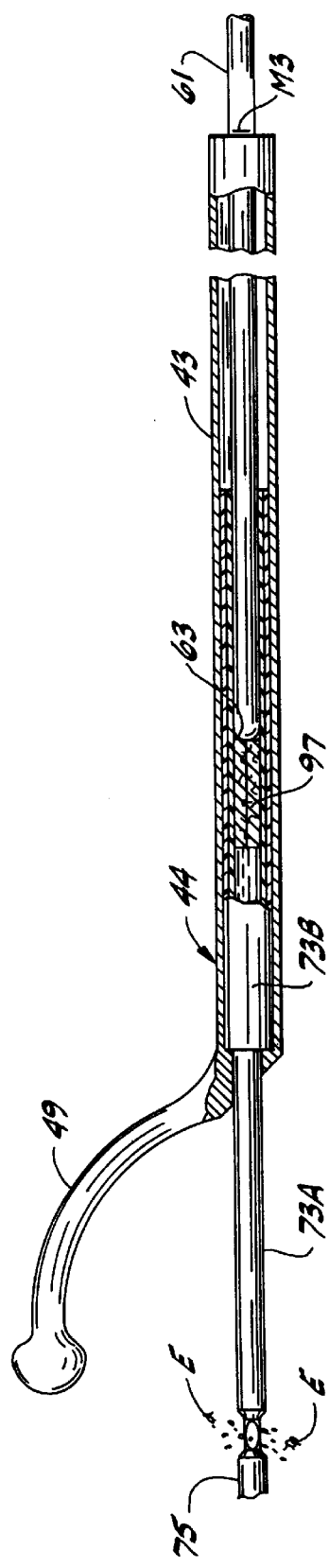

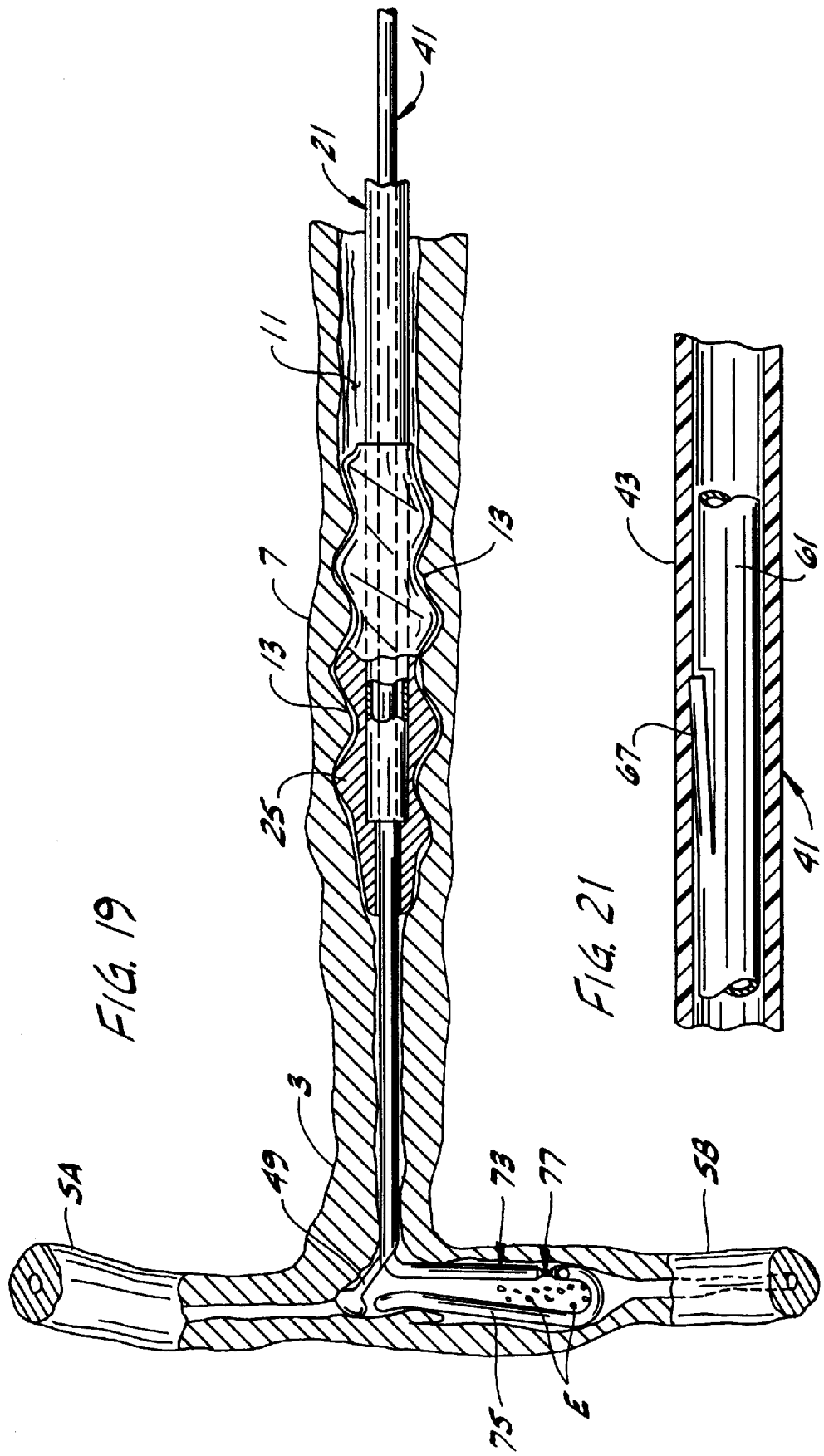

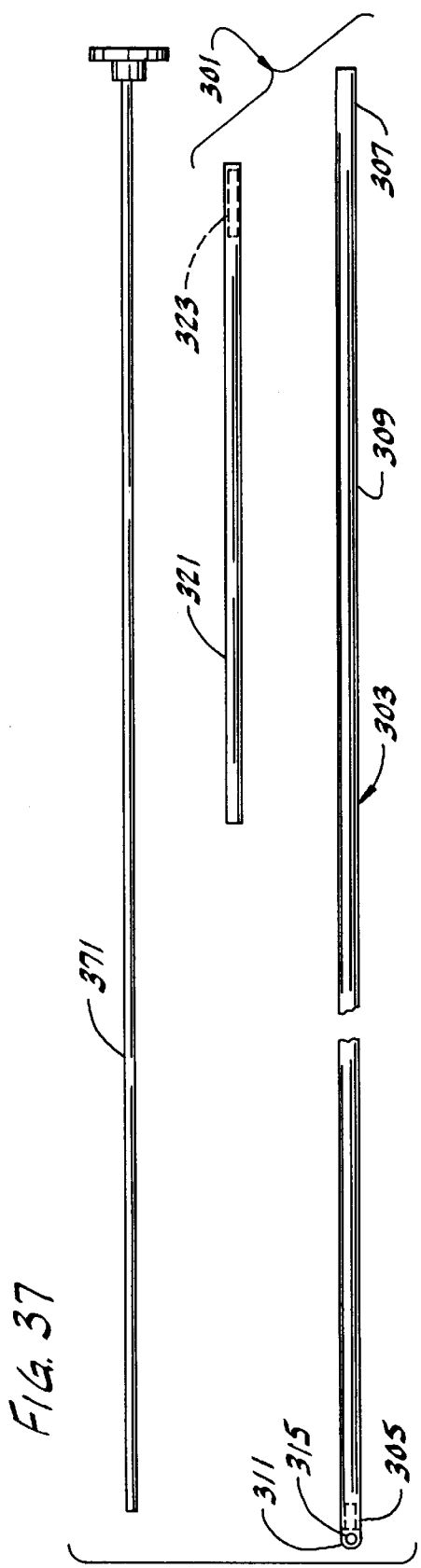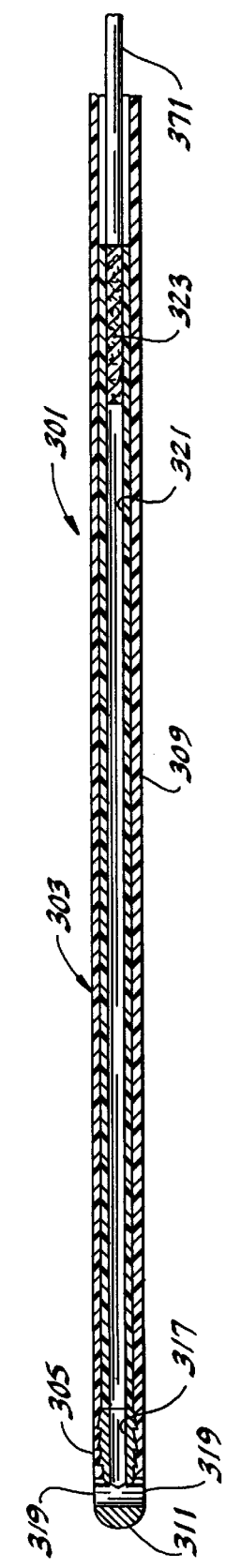

SYSTEM FOR INTRODUCING A FLUID INTO THE UTERUS OF AN ANIMAL

This application is a continuation-in-part of U.S. patent application Ser. No. 08/438,174, filed May 9, 1995, which issued as U.S. Pat. No. 5,558,636 on Sep. 24, 1996 and is also a continuation-in-part of U.S. patent application Ser. No. 08/438,162, filed May 9, 1995, which issued as U.S. Pat. No. 5,656,010 on Aug. 12, 1997.

SUMMARY OF THE INVENTION

This invention relates generally to the nonsurgical transfer of fluid comprising semen or a fluid medium containing embryos into the uterus of an animal, such as a pig or cow.

The nonsurgical transfer of embryos from a female donor animal to a female recipient animal has been employed for many years to achieve the genetic improvement of breeds. In the porcine industry, attempts at nonsurgical embryo transfer have met with only limited success. This is due in large part to physiology. The cervical structure of a female pig is such that it is a barrier to nonsurgical methods of transfer.

One attempt at a non-surgical embryo transfer is described by J. M. Galvin et al. in "Theriogenology" 41:1279–1289, 1994. The described procedure involves inserting a tubular instrument (spirette) into the cervix of a recipient pig, and then forcing 10–12 milliliters of liquid medium containing embryos into and through the instrument, the objective being to deposit the embryos in the uterus. However, this procedure has several serious drawbacks. First, there is no way to determine whether the instrument has been inserted far enough into the cervix so that its forward end is adjacent the body of the uterus. As a result, in instances where the forward end of the instrument remains lodged within the cervix, the embryos may never reach the uterus. Also, if the instrument is inserted too far, the uterus or surrounding tissue may be damaged. Another disadvantage of this procedure is that the relatively large quantity of liquid introduced into the cervix and uterus tends to make the uterine environment unsuitable for growth of the embryos.

The non-surgical transfer of embryos into bovine has also been less than entirely successful. In one widely used conventional system, a disposable embryo transfer cannula is used. One such cannula is made in France by IMV L'aigle. It consists of a long straight piece of tubing (21 in. long) with an outer diameter of 0.14 in. The cannula has a polished front tip with two embryo release openings in the tip. The cannula is manipulated through the vagina, cervix and part of the uterine lumen of a cow during embryo transfer. Due to anatomical variations among different individual cows in age, breed and physical status, difficulties are often encountered in passing the cannula through the bovine cervix. Using excessive force may severely irritate or even damage the genital tract, causing the transplant to fail. The embryos to be transferred can also be easily trapped in mucus which collects on the tip of the cannula as it is moved forward through the cervix.

As a result of the aforementioned problems, the success rate in bovine embryo transplant is only about 60%. As a result, the dairy and beef industries have suffered millions of dollars in annual losses due to the cost of maintaining the non-pregnant recipient animals.

Conventional artificial insemination (AI) techniques in the bovine industry also provide a pregnancy rate of only about 60%. This is also due to the difficulty associated with passing a conventional straight AI cannula through the bovine cervix, and the collection of mucus on the cannula which hinders the successful transfer of semen into the body of the uterus.

There is a need, therefore, for an improved system for effecting the nonsurgical transfer of embryos into recipient animals, particularly those having a cervix of the type which is difficult to penetrate, such as pigs and cows. There is also a need for an improved system for effecting the artificial insemination of bovine and possibly other animals.

Among the several objects and features of the present invention are the provision of an improved system for transferring fluid comprising semen or a fluid medium containing embryos into a recipient animal; the provision of such a system which ensures that the fluid being transferred is deposited in the proper location in the uterus of the recipient animal, even though the cervix of the animal has an anatomical design which is difficult to penetrate; the provision of such an improved system which minimizes the risk of contamination, trauma and injury to the animal during the transfer procedure; the provision of such a system which, when used to transplant embryos, effects such transfer with only a minimal amount of liquid medium so as not to disturb the natural environment of the uterus of the recipient animal; the provision of such a system which is easy to use and which effects the transfer very quickly and efficiently; the provision of such a system which is sanitary; the provision of such a system which results in an increased rate of pregnancy compared to prior procedures, and which results in litters of larger size; and the provision of such a system which is relatively inexpensive to manufacture.

In general, a system of this invention is useful for penetrating the uterus of an animal during a nonsurgical procedure, the uterus having a cervix leading to a uterus body. The system comprises a probe having a long tubular body with a central longitudinal axis, open forward and rearward ends, and a probing member projecting forward and laterally outward substantially beyond the forward end of the probe body. The probe is adapted to be inserted, forward end first, inside the cervix of said animal. The probe body is manipulatable to gently maneuver the probing member in a forward direction through the cervix to a position in which the probing member and the forward open end of the probe body are adjacent the body of the uterus.

This invention also relates to an improved method of effecting the non-surgical introduction of fluid comprising either semen or a fluid medium containing embryos into the uterus of an animal. The method involves the use of a probe having a long tubular body with a central longitudinal axis and an open forward end, and a probing member on the probe body projecting forward and laterally outward beyond the forward end of the probe body. The method comprising the steps of inserting the probe, forward end first, into a cervix of the uterus of the animal, and pushing the probe in a forward direction while simultaneously rotating the probe body about its central longitudinal axis to cause said probing finger to gently maneuver through the cervix until the probe is in a forward position in which the forward end of the probe is in the uterus of the animal. The method also involves placing a fluid carrier carrying fluid inside the probe body and, after the probe is in its said forward position, releasing fluid from the carrier into the uterus.

Other objects and features will be in part apparent and in part pointed out hereinafter.

BRIEF DESCRIPTION OF THE DRAWINGS

FIG. 2 is an elevation of a gripping instrument of the system of this invention;

FIG. 3 is an enlarged view of front and rear end portions of the instrument of FIG. 2;

FIG. 4 is an elevation of a probe of the system;

FIG. 5 is an enlarged view of a front end portion of the probe of FIG. 4;

FIG. 6 is a left end view of FIG. 5;

FIG. 7 is an elevation of a testing bar of the system;

FIG. 8 is an enlarged view of a part of the testing bar of FIG. 7;

FIG. 9 is a view of an embryo carrier of the system;

FIG. 10 is an enlarged view of part of the carrier of FIG. 9;

FIG. 11 is a view similar to FIG. 10, portions of the carrier being broken away to illustrate details;

FIGS. 12–15 are views illustrating how embryos are loaded into the carrier;

FIGS. 16–20 are views illustrating how the embryos are transferred to the uterus of a pig;

FIG. 21 is a view illustrating how the carrier is removed from the uterus after the embryos have been transferred;

FIG. 37 is a view showing various components of a carrier comprising a conventional embryo transplant "gun";

FIG. 38 is a view illustrating part of an assembly of the components of FIG. 37;

Corresponding parts are designated by corresponding numerals throughout the several views of the drawings.

DESCRIPTION OF THE PREFERRED EMBODIMENT

The drawings illustrate a system of this invention for effecting the nonsurgical transplant (transfer) of fluid comprising either semen or a fluid medium containing embryos into the uterus of an animal. This system is particularly applicable to the transplant of embryos into pigs and bovine, and to the artificial insemination (AI) of bovine, but it will be understood that it may also be used to carry out AI and/or nonsurgical embryo transfers in other animals.

Figure 1:
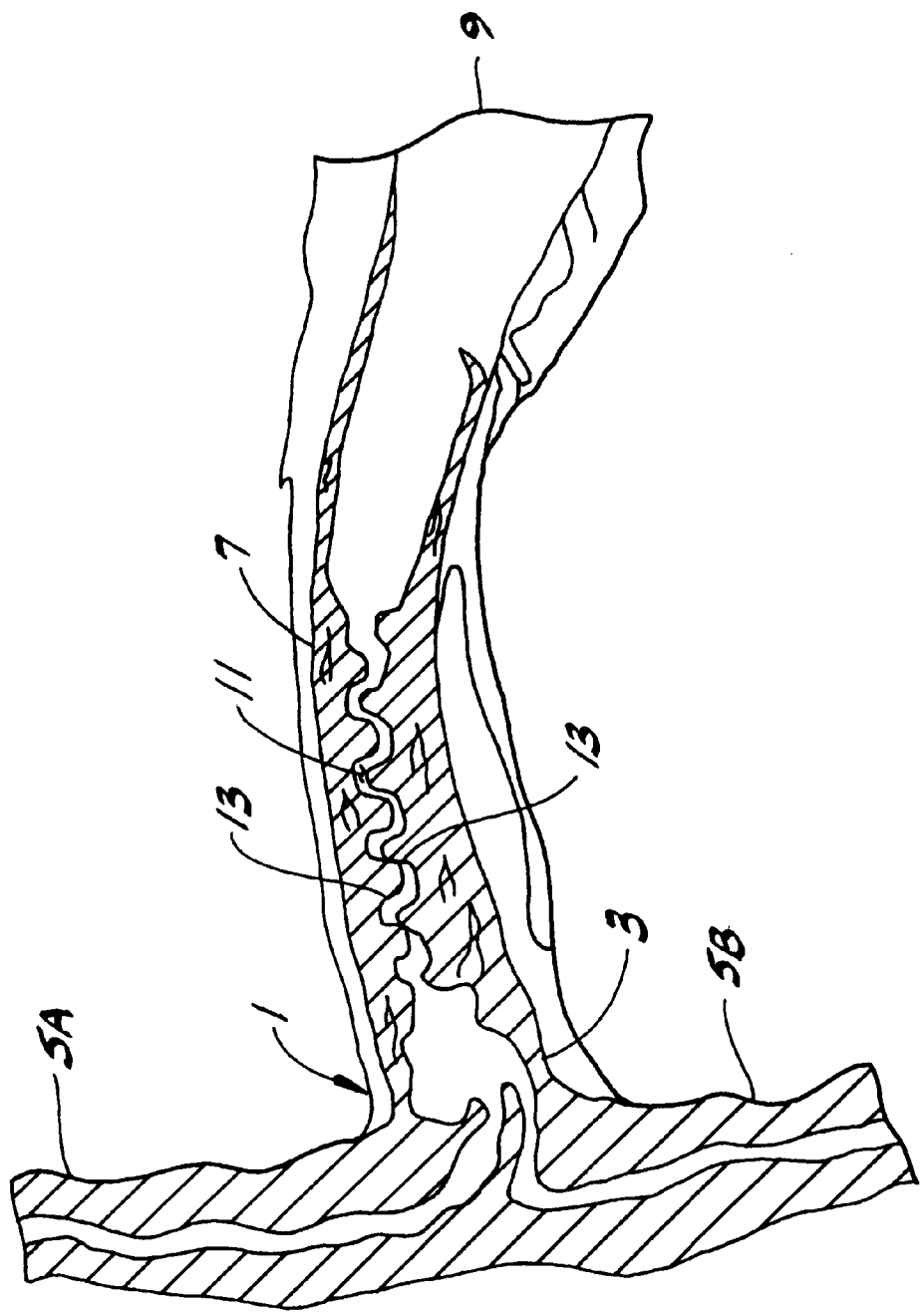
FIG. 1 is a schematic illustration of the uterus of a pig.

For purposes of illustration, FIG. 1 shows the anatomical configuration of the uterus of a pig. The uterus (which is generally designated 1) comprises a uterus body 3, a pair of horns 5A, 5B extending from the body, and a cervix 7 connecting the vagina 9 of the pig to the body 3 of the uterus. The inside walls defining the cervical canal 11 of the cervix are convoluted and lined with rounded prominences 13, some of which dovetail to occlude the canal. It is this anatomy which has hindered prior attempts to effect the non-surgical transfer of embryos.

One embodiment of a system of this invention useful in the nonsurgical transplant of embryos in pigs, for example, includes five parts, the first of which is shown in FIG. 2. It comprises a gripping instrument, generally designated 21, having a long tubular body 23, an external gripping formation in the form of a screw (spiral) head 25 at the forward end of the body 23, and a handle 27 at the rearward end of the body formed with a series of ribs 29 to facilitate grasping and turning the instrument on its longitudinal axis. As shown in FIG. 3, both the screw head 25 and the handle 27 have bores in axial alignment with the bore through the body to provide a continuous passage 35 through the entire assembly from the rearward end of the handle to the tip of the screw head. The body 23, head 25 and handle 27 of the instrument 21 can be molded plastic parts, with the head being of a soft flexible material so as not to injure the animal when the instrument is inserted, head first, into the cervix, as will be described later. A suitable instrument of this type is commercially available from Swine Genetics International located in Cambridge, Iowa.

The second part, shown in FIG. 4, comprises a probe generally indicated at 41 having a long tubular 43 body with open forward and rearward ends indicated at 45 and 47, respectively, and a probing member comprising a slender, finger-like member 49 (or, more simply, a finger) projecting in an non-axial direction from the probe body generally adjacent its forward end. More specifically, as illustrated in FIGS. 5 and 6, the finger 49 curves or arcs in spiral fashion laterally outwardly and forwardly from the probe body substantially beyond its forward end, the arc A shown in FIG. 5 being centered on a point P1 generally in-line with the probe body, and the arc B shown in FIG. 6 being centered on a point P2 generally in-line with the central longitudinal axis 51 of the probe body. The finger has a blunt and enlarged forward end indicated at 53. The probe body 43 and finger 49 are preferably formed as a single piece of metal, such as stainless steel, but may also be formed of plastic. The diameter of the finger 49 is preferably 0.05–0.15 in., while the diameter of the enlarged forward end 53 may be 0.1–0.2 in. Additionally, the length of the arching finger 49 is preferably 0.4–0.8 in. and the laterally outward projection of the finger from the central longitudinal axis 51 of the probe body 43 may be 0.2–0.45 in. By way of example, arc A may have a radius of about 0.43 in. and arc B may have a radius of about 0.5 in. The probe body may be formed from 12-gage hypodermic stainless steel tubing having an outside diameter of 0.109 in. and an inside diameter of 0.085 in. The length of the probe body may range from 16 in. to 28 in. For reasons which will become apparent hereinafter, the forward end 45 of the probe body is formed with an internal annular shoulder 55 forming an abutment (the inside diameter of the probe body rearward of this shoulder or abutment may be 0.109 in., for example, and the inside diameter of the probe body forward of this abutment may be 0.075 in., for example).

The probe 41 is sized to be slidably inserted, rearward end first, into the forward (head) end of the gripping instrument 21. It also has a length considerably longer than the gripping instrument so that, when fully inserted into the instrument, the rearward end 47 of the probe projects endwise beyond the rearward end of the instrument. By way of example, the gripping instrument 21 may have an overall length of 17.8 in., and the probe 41 may have an overall length of about 25.6 in. Thus, the rearwardly projecting end of the probe serves as a handle by which the probe may be grasped to manipulate the probe to rotate it and to move it forward and rearward relative to the gripping instrument from a fully retracted position in which the probing finger 49 is retracted inside the soft flexible head 25 of the instrument, and an extended position in which the probing finger is forward of the head 25 for probing through the cervix, as will be described later.

The third part of the system is shown in FIG. 7 as comprising a long slender testing or detecting bar 61, preferably of round stainless steel bar stock having a rounded and polished forward end 63 (left end as viewed in FIG. 7). The bar is sized to be slidably inserted, forward end first, into the rearward end 47 of the probe body 43, and to be pushed forward so the forward end of the bar extends beyond the forward end 45 of the probe body 43 and beyond the tip 64 of the probing finger 49. The bar 61 is longer than the probe body so that when fully inserted into the probe body, the bar extends rearwardly from the probe body so that it may be grasped to move the bar back and forth relative to the probe body. By way of example, the bar 61 may have a diameter of 0.0625 in. and a length of 28 in. The rearward end 65 of the bar (e.g., the rearwardmost 1.0 in. of the bar) is enlarged to form a pusher. This pusher, the function of which will become apparent later, has a diameter (e.g., 0.083 in.) only slightly less than the inside diameter of the probe body 43. To facilitate proper use of the bar 61, it is marked as indicated at M1 with a first score line or the like to indicate visually when the forward end of the bar is coterminal with the forward end 45 of the probe body 43, and as indicated at M2 and M3 with second and third score lines or the like to indicate visually when the forward end of the bar projects predetermined distances (e.g., 1 in., and 2 in.) beyond the forward end of the probe body.

The testing bar 61 is formed to have a flexibly resilient tongue 67 spaced rearwardly (e.g., about 3.0 in.) from the forward end 63 of the bar. This tongue 67 is biased toward the position shown in FIG. 8 so that its rearward (free) end projects laterally outwardly from the bar. The purpose of this tongue will also become apparent later.

The fourth part of the system, shown in FIGS. 9–11, is an embryo carrier, generally designated 71, comprising a tubular member 73, a long flexible guide member 75 forward of the tubular member, and a ported member generally indicated at 77 connecting the tubular member 73 and the guide member 75 in axial alignment. By way of example, the guide member 75 may be formed from a 3.0-in. length of plastic leader tubing having a closed polished forward end 78, an OD of 0.06 in. and an ID of 0.035 in. As shown in FIG. 10, the ported member 77 has a forward end part 79 sealingly press fitted in the rearward end of the guide member 75, a rearward end part 81 sealingly press fitted in the open forward end of the tubular member 73, and a center part 83 having a port 85 therein. This port is disposed between the spaced apart ends of the guide member 75 and the tubular member 73 so that it is exposed.

The forward end 79 part of the ported member 77 is closed to block any flow of fluid therethrough, and the rearward end 81 part of the ported member has a passage 87 which communicates with the aforesaid port 85. By way of example, the ported member 77 may be formed by a length of stainless steel hypodermic tubing (20-gage, thin wall), and a stainless steel stopper 89 plugging the forward end part 79 of the member. Opposing portions of the side wall of the tubing are removed as shown in FIGS. 10 and 11 to form opposing apertures 91A, 91B in the tubing. These apertures combine to form the aforementioned port 85. As will be described later, the port functions as an inlet through which embryos can enter the carrier 71 and as an outlet through which the embryos can exit into the uterus.

The tubular member 73 may be fabricated from two lengths of tubing, the first being indicated at 73A and the other at 73B. The first piece is of smaller diameter than the second piece and is press fitted into the second piece to form a single tube having a shoulder 95 constituting an external stop at the intersection of the two pieces. By way of example, piece 73A may be a length of semi-flexible plastic tubing having an OD of 0.06 in., an ID of 0.04 in. and a length of 4.0 in., and piece 73B may be a length of hard plastic tubing having an OD of 0.083 in., an ID of 0.0625 in., and a length of 5.25 in. The connection between the two pieces of tubing should be a sealing connection.

A plug 97 of absorbent expandable material (e.g., cotton) is received in the rearward end of the tubular member. This plug is initially annular in shape with a passage 99 through it to permit aspiration of embryos into the carrier by means of an aspirator connected to the rearward end of the tubular member 73B. During such aspiration, this plug 97 expands to close and seal the rearward end of the tubular member, as will be explained later.

The fifth and final part of the system comprises a two-part sheath, generally designated 101, protecting and sealing the embryo carrier 71. The sheath comprises front and back parts designated 103 and 105, respectively, both of which are formed from tubes of plastic, for example, the front end of the front part being closed by a permanent plug 107 and the back end of the back part 105 being open. The back end of the front part is recessed and chamfered as indicated at 109 for receiving the front end of the back part 105 to form a press-fit, sealing connection between the two sheath parts. The front tubular part 103 of the sheath should have a length and inside diameter sufficient to house the guide member 75 and ported member 77 of the carrier, and the back tubular part 105 of the sheath should have a length and inside diameter sufficient to house the tubular member 73 of the carrier.

The use of the system described above is described below in connection with the transplant of embryos in a pig.

The first step in the method of this invention is to sterilize all parts of the system to reduce the risk of contamination during the embryo transfer. Following sterilization, the gripping instrument 21, probe 41 and bar 61 should be preassembled and packed into a plastic bag to avoid contamination. As previously described, this is achieved by inserting the probe, rearward end first, into the forward end of the gripping instrument, and by inserting the bar, forward end first, into the rearward end of the probe.

Step two is to load the embryos into the carrier 71. The preferred methodology, illustrated in FIGS. 12–15, involves submerging the port member 77 of the carrier in a suitable fluid culture medium (e.g., TL-Hepes) held in a cup-like receptacle or dish 111 having a bottom 113 and a circular side wall 115 extending up from the bottom. This can be accomplished by first inserting the two-part sheath 101, with the carrier 71 inside, through aligned openings 117 in the side wall 115 of the dish, the fit of the sheath in these openings being sufficiently tight to form a seal. Culture medium suitable for the embryos to be transferred is then deposited in the dish, and the two parts of the sheath are separated to expose the apertures 91A, 91B in the port member 77 (FIGS. 12 and 13).

Using a suitable aspirator, such as a syringe (indicated at 121 in FIG. 12), connected to the open rearward end of the back part 105 of the sheath 101 such that it forms a seal with the rear end of the piece 73B of the tubular member 73, a predetermined quantity of fluid (e.g., 0.3 ml.) is aspirated into the tubular member of the carrier 71 through the apertures 91A, 91B in the ported member, the apertures thus constituting an inlet of the carrier during this stage of the procedure. No air bubbles should be trapped in the tubular member 73 during this stage of the loading procedure. After the aforesaid predetermined quantity of fluid has been aspirated, the ported member 77 is raised above the fluid in the dish 111 to aspirate a first air bubble 123 into the tubular member 73 (FIG. 14), following which the ported member 77 is resubmerged in the medium. Embryos E are then introduced into the medium by means of a pipette, for example, at a location immediately adjacent the carrier inlet 85, so that they are aspirated along with the medium into the tubular member 73 of the carrier 71. After the embryos have entered the carrier, a second air bubble 125 is aspirated into the carrier so that the embryos are trapped between the two air bubbles (FIG. 14). Following this process, an additional quantity of fluid (e.g., 0.1 ml.) is aspirated into the carrier. This quantity should be sufficient to fill the tubular member 73 to a point where liquid comes into contact with the absorbent plug 97 at the rearward end of the tubular member. Upon absorption of this liquid, the plug expands to close the passage 99 through it, thereby sealing the rearward end of the carrier. The aspirator can then be disconnected and a stopper 123 inserted in the back part 105 of the sheath 101.

After the aspiration is complete, the two parts 103, 105 of the sheath can be pushed together to provide a sealed enclosure for the entire carrier 71 and the embryos E in it. At this point, the sheathed carrier can be transported to the site where the embryo transfer is to take place. The sheath 101 serves two functions, namely, to prevent evaporation of the culture medium carrying the embryos, and to maintain the sterility of the carrier prior to transfer of the embryos into the recipient animal. It should be noted in this regard, that the aforementioned procedures, during which the embryos were loaded into the carrier, should be carried out under sterile conditions.

The next step in the process is to anaesthetize the recipient animal prior to beginning the actual embryo transfer process. Preferably, the animal should be fully anaesthetized prior to start of this process.

After anaesthetization, lubricant (e.g., a water-based non-toxic lubricant) is applied to the vagina of the recipient animal, and also to the gripping instrument 21, probe 41 and bar 61. With the probe and bar fully retracted inside the gripping instrument to minimize the risk of contamination, the instrument 21 is inserted, screw head 25 first, into the vagina of the animal. This should be done by pushing the instrument forward while rotating the instrument in a counterclockwise direction. This will cause the instrument to advance into the cervix 7 of the animal and to obtain a firm grip or lock on the walls of the cervix, which as mentioned previously, are formed with rounded interdigitated prominences 13.

When a firm cervix lock has been established, the gripping instrument 21 is pulled rearwardly to tension and thus straighten the convoluted configuration of the cervix (see FIG. 16). The probe 41 should then be pushed forward very gently beyond the forward end of the gripping instrument to a point where there is significant resistance to further movement (FIG. 17). Encountering such resistance means either that the probe is still positioned inside the cervix or that it has been moved through the cervix and is against the forward end of the body of the uterus. To determine which, the testing bar 61 inside the probe 41 should be pushed forward very gently until a significant resistance is felt, after which the probe should be pulled rearwardly a predetermined distance (e.g., approximately one inch) in relation to the gripping instrument. If the bar 61 can move freely back and forth relative to the probe 41 within a predetermined range of movement (e.g., between marks M1 and M2 on the bar relative to the rearward end of the probe), then the forward end of the probe is likely through the cervix and positioned inside the body 3 of the uterus. Otherwise, the probe is still in the cervix. In the latter situation, the probe 41 should be manipulated to turn the probing finger 49 while pushing the bar 61 gently forward, and while pulling the gripping instrument 21 rearwardly. The combination of these actions tends to work and maneuver the probe through and past the occluding protrubernances in the cervix. (The curved, spiral configuration of the probing finger 49 causes it to thread through the cervical canal, like a screw, when the probe is rotated.) This process is carried out until the finger 49 of the probe is through the cervix and positioned in the body of the uterus, as determined by using the bar 61 in the manner described above.

After the forward end 45 of the probe is positioned in or generally adjacent the body 3 of the uterus, the carrier 71 is removed from its sheath 101 and inserted, guide end first, into the open rearward end of the probe 41 (the testing bar 61 having first been removed). The bar 61 is then inserted, pusher end first, into the probe 41 and used to push the carrier forward to a point where the external stop 95 on the carrier engages the internal abutment 55 at the forward end of the probe. This point can be visually confirmed by the use of a score line M4 or the like (see FIG. 7). (When the bar 61 is pushed to a point where score line M4 is at the rearward end of the probe body 43, the stop 95 is in engagement with the abutment 55.) As the carrier moves forward, the long flexible guide member 75 guides the carrier into the lumen of one of the horns 5A, 5B of the uterus to position the ported member 77 of the carrier for release of the embryos E inside the horn, which is the preferred location of release. As illustrated in FIG. 19, the flexible guide member 75 typically forms a loop in the horn of the uterus, which eliminates the possibility of penetrating the highly proliferated lumen epithelial membrane.

Insertion of the carrier into the horn of the uterus should not meet substantial resistance. Substantial resistance indicates that the probe 41 is still in the cervix, not in the body of the uterus. If substantial resistance is encountered, the carrier should be removed and the process described above should be repeated to move the probe to a position where it is in the uterus.

After the carrier 71 is positioned in the horn, the bar 61 is removed from the probe 41, reversed again, and reinserted, forward end first, into the probe. The forward end 78 of the bar 61 has an outside diameter less than the inside diameter of the rearward piece 73B of the tubular member 73 of the carrier, the arrangement being such that the front end of the bar is adapted to enter the tubular member 73 and to push the closed plug 97 forward in the tubular member to a point where the mark M3 on the bar generally aligns with the rearward end of the probe (see FIG. 20). This serves to eject a predetermined amount of fluid (e.g., 0.3 ml.), including the medium containing the embryos, through the outlet 85 of the carrier and into the horn of the uterus. During this process, the carrier is held against forward movement by the abutment of stop 95 against the internal shoulder 55 on the probe. The ejection of the embryos should be effected slowly. The presence of the air bubbles 123, 125 on opposite sides of the slug of medium carrying the embryos ensures that the embryos do not adhere to the walls of the carrier during the ejection process. The total amount of liquid ejected into the uterus during this process is less than 10 ml., preferably less than 1.0 ml., and most preferably about 0.3 ml.

After the embryos are transferred, the bar 61 is pulled rearwardly, which causes the tip of the tongue 67 formed on the bar to bite into or otherwise catch the piece 73B of the tubular member 73 of the carrier (FIG. 21). Consequently, movement of the bar 61 in a rearward direction also pulls the carrier 71 in the same direction to remove the carrier from the uterus. The bar and carrier should be retracted to a position in which the carrier is completely inside the probe 41. The probe should then be pulled slowly rearwardly while rotating it gently in a clockwise direction to a point where the probing member 49 is adjacent or fully retracted inside the head 25 of the gripping instrument 21. Following this, the gripping instrument may be turned clockwise to remove all parts out of the vagina. The carrier 71 is then discarded; the gripping instrument, probe and bar are reusable after sterilization. Alternatively, the carrier may also be reusable.

To minimize irritation and to avoid injury during this transfer process, the probe and bar should be manipulated very gently. They should never be forced through substantial resistance.

The system and methodology as described above have been successfully employed. Embryos (from the 4-cell stage to the blastocyst stage) have been surgically collected from either naturally cycling or superovulated donor pigs on day 5 after estrus via and cultured in TL-Hepes up to 5 hours before the non-surgical embryo transfer. The recipients were either naturally cycling or superovulated gilts on day 4 or 5 after onset of estrus, and had from two to five post-pubertal estrous periods. All of the experimental females were checked for estrus daily by exposing them to a mature boar. Five recipients became pregnant out of a total of sixteen nonsurgical embryo transfers (31.25%). Four recipients farrowed and their litter sizes were 5,9, 3 and 10, respectively, with an average of 6.8±3.3 pigs per litter.

The success of the system and methodology described above are believed to be due to several factors. First, the system and method ensure that the embryos will be released not in the cervix, but rather in the body of the uterus, preferably in the lumen of one uterine horn where they will have the best chance of successful gestation. Successful penetration through the cervical canal, and sensing when this occurs, is made possible by the unique probe 41 of this invention, particularly when used in combination with the testing or detecting bar 61. Second, the embryos are introduced in the uterus with only a minimum of accompanying fluid (most preferably only about 0.3 ml.), so that the uterine environment is not significantly altered from its natural state, which is most suitable for gestation. And third, the process minimizes the risk of trauma, contamination and injury to the animal.

Figure 22:
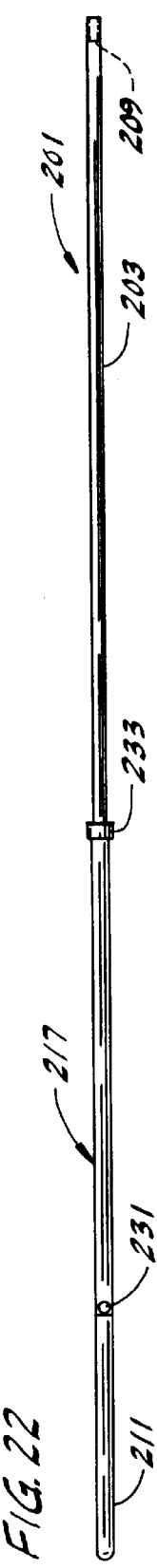
FIG. 22 is a view of an alternative carrier of the present invention.
Figure 22A:
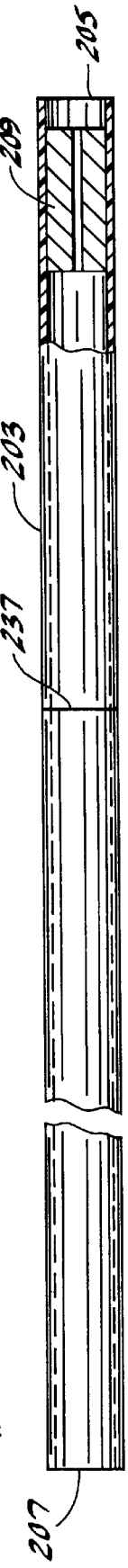
FIG. 22A is a view of a straw component of the carrier of FIG. 22, a portion of straw being removed to show details.

An alternative carrier, generally indicated at 201, is illustrated in FIGS. 22–26. As shown in FIGS. 22 and 22A, the carrier 201 comprises a tubular straw 203 of plastic tubing, such as clear 14-gage plastic tubing having an outside diameter of 0.083 in., and inside diameter of 0.06 in., and a length of 7.5 in., corresponding to a standard commercial ¼ cc embryo transfer straw except somewhat longer to hold more fluid medium. The straw 203 has an open rearward end 205 for connection to an aspirator and an open forward end 207 for aspiration of a fluid medium containing embryos into the straw. An absorbent expandable plug 209 similar to plug 97 described above is located in the rearward end of the straw.

Figure 23:
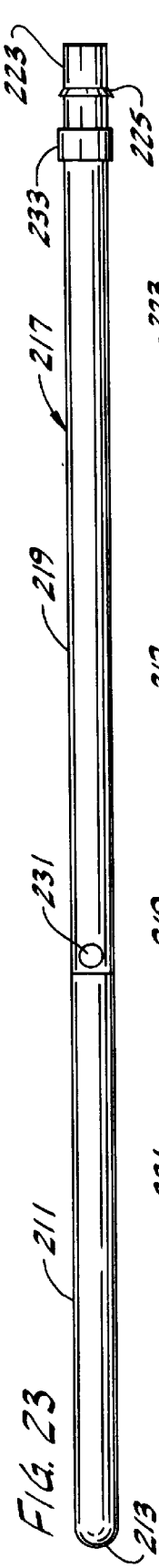
FIG. 23 is a view of additional components of the alternative carrier, including a guide member and a connector for connecting the guide member to the straw component of FIG. 22A.

The carrier 201 also includes a long flexible guide member 211 (similar to guide member 75) for guiding the carrier into a fluid release position in the body of the uterus (FIG. 23.) The guide member is preferably made of soft leader tubing of Tygon, silicon rubber, Viton, polyurethane, or other suitable material. The tubing may have an outer diameter of about 0.083 in., an inside diameter of about 0.063 in., and a total length of about 1.5 in. The front tip 213 of the guide member is polished to reduce the risk of damage to the vulnerable lumen membrane.

Figure 24:
FIG. 24 is an enlarged view of the connector with portions broken away to show an outlet port.

The carrier further comprises a tubular connector, generally designated 217, for connecting the guide member 211 to the open front end of the straw 203. The connector 217 is made of semi-hard plastic tubing, such a Nylon or polyethylene tubing having an outside diameter of 0.083 in. and an inside diameter of 0.05 in., and is best shown in FIG. 24 as having a body 219 and forward and rearward end parts 221, 223, each end part being formed with an integral locking shoulder 225. The end parts 221, 223 are slidably insertable in the rearward end of the guide member 211 and the forward end of the straw 203, and the locking shoulders 225 are engageable with the guide member and straw to make the connections secure. The body 219 of the tubular connector between the end parts preferably has a length of about 3 in., although this dimension may vary. An outlet port comprising a pair of diametrically opposite apertures 231 in the body 219 of the tubular connector adjacent its forward end are in fluid communication with the open forward end 207 of the straw 203 for release of fluid inside the straw through the outlet port 231, as described below.

The body 219 of the connector 217 is formed with an annular stop 233 adjacent its rearward end. The purpose of this stop is to engage the internal annular shoulder 55 on the probe 41 to limit the forward movement of the carrier 201 relative to the probe. The stop 233 on the connector body is so located that when it engages the internal shoulder on the probe, the guide member 211 and much of the connector 217, including the outlet port 231, are disposed forwardly beyond the forward open end of the probe body 43 for release of fluid at the proper location in the uterus, as described above.

Figure 26:
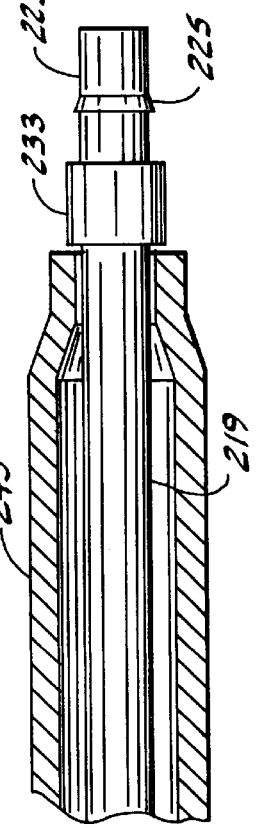
FIG. 26 is a view showing part of the straw component filled with fluid prior to connection to the connector of FIG. 24.
Figure 25:
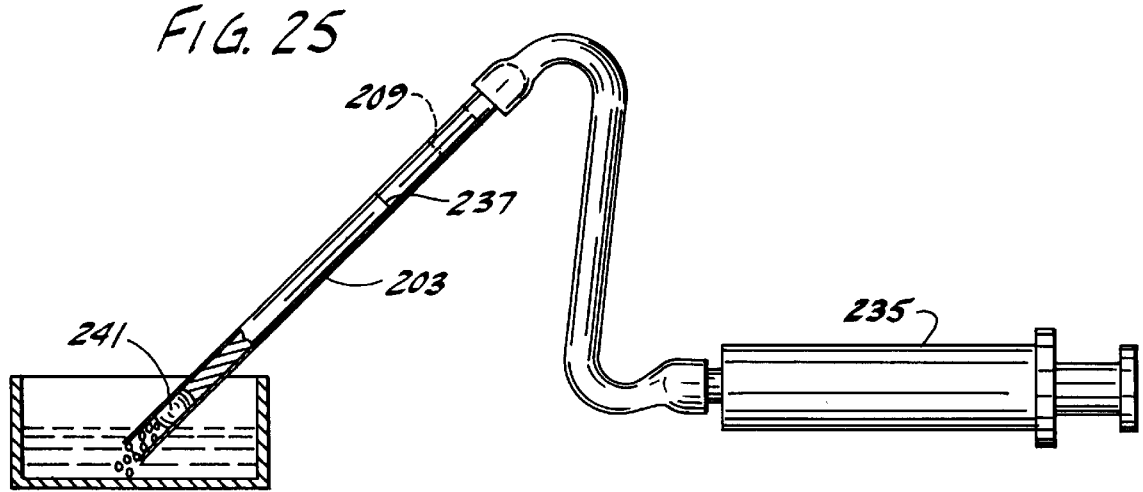
FIG. 25 is a view showing how fluid is loaded into the straw component.

A carrier of this type is very easy to use, as illustrated in FIGS. 25 and 26. To load the carrier, an aspirator 235 is connected to the rearward end of the straw 203 and fluid transfer medium is aspirated into the straw to partially fill it (e.g., to a mark 237 indicating that the straw is 80% filled). An air bubble 241 is then aspirated into the straw, after which fluid medium containing embryos 243 is aspirated into the straw until the plug 209 is wetted and expands to close the rearward end 205 of the straw. The forward end 207 of the straw is then pushed onto the rearward end part 223 of the connector 217 until it seats against the stop 233, thereby connecting the straw to the flexible guide member 213 connected to the opposite end of the connector (FIG. 26). The carrier is then ready for the non-surgical embryo transplant process described above. A suitable plastic cover 245 (partially shown in FIG. 26) can be used to protect the connector 217 and guide member 211 during the connection procedure and further handling prior to embryo transfer.

A widely used bovine AI semen straw suitable for use as straw 203 is 5.25 in. long with an outside diameter of 0.109 in. and an inside diameter of 0.085 in. If this particular straw is used as part of the carrier 201, it will be understood that the dimensions of the probe 41, bar 61 and other components of the system should be varied accordingly. For example, under these circumstances the probe body 43 may be made from stainless steel tubing having an inner diameter of 0.128 in. (9 gage tubing) or 0.135 (8 gage tubing) and an outer diameter of 0.148 in. (9 gage tubing) or 0.165 (8 gage tubing) so that the straw 203 will readily fit into the probe.

Figure 27:
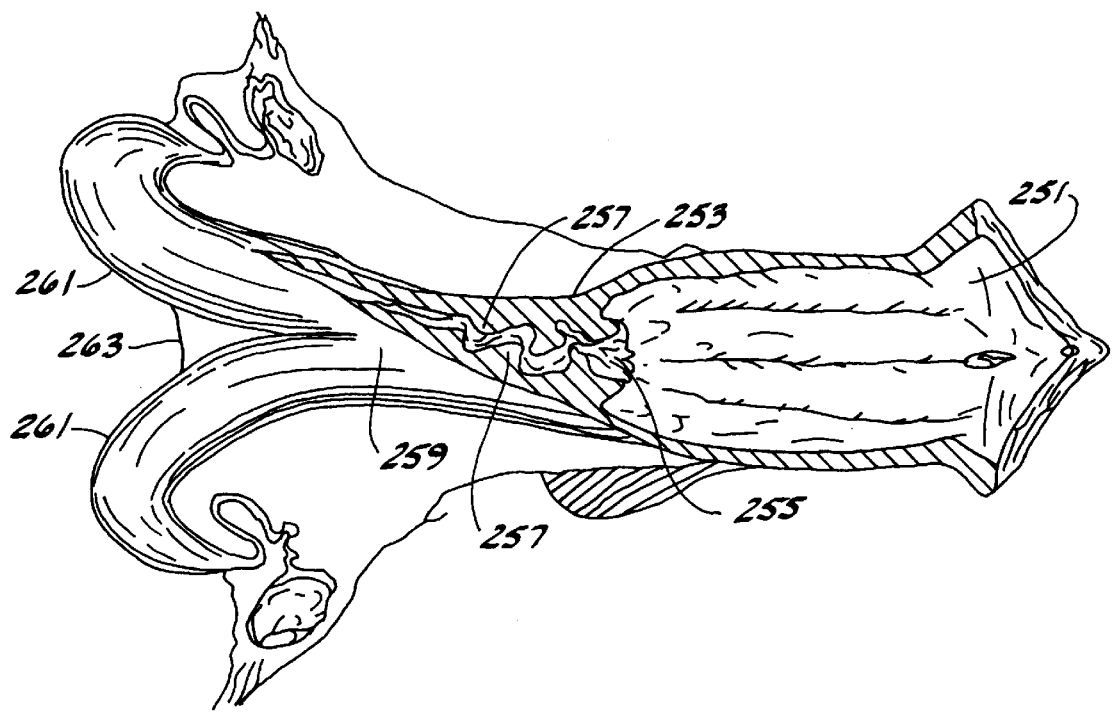
FIG. 27 is a view of a bovine genital tract.
Figure 28:
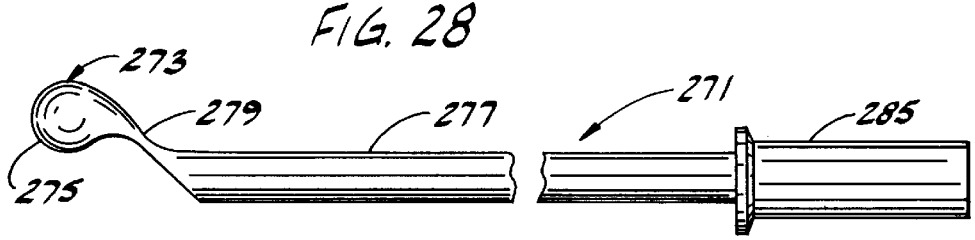
FIG. 28 is a side elevation of a probe of this invention for use in connection with bovine embryo transplant and artificial insemination.

The system of the present invention can also be employed for AI or embryo transplant in bovine. FIG. 27 illustrates the genital tract of a cow, including a vagina 251 and a cervix 253 having a uterine orifice 255 and plicae circulares 257 which are interdigitated with one another to obstruct the cervical canal. The body 259 of the uterus is located between the cervix 253 and the uterine horns 261 which are connected by a dorsal intercornual ligament 263. The edge of this ligament is an indicator for a safe embryo deposit. (The embryos should be deposited forward beyond the ligament 263 in the lumen of the horn 261 connected to the most recently ovulating ovary.)

Figure 29:
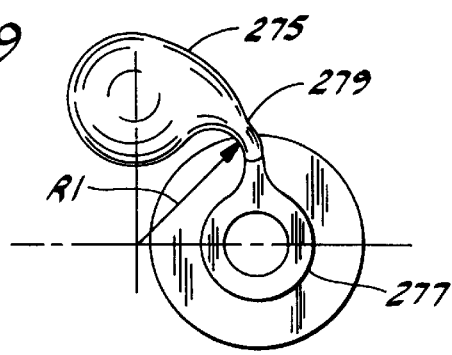
FIG. 29 is a left end view of FIG. 28.
Figure 30:
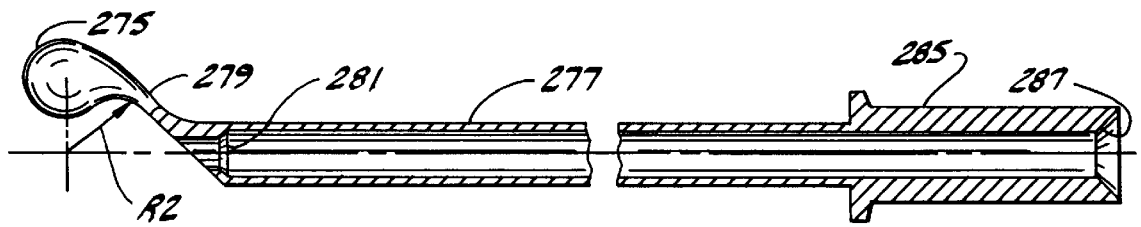
FIGS. 30 and 31 are sectional views of the probe of FIG. 28.
Figure 31:
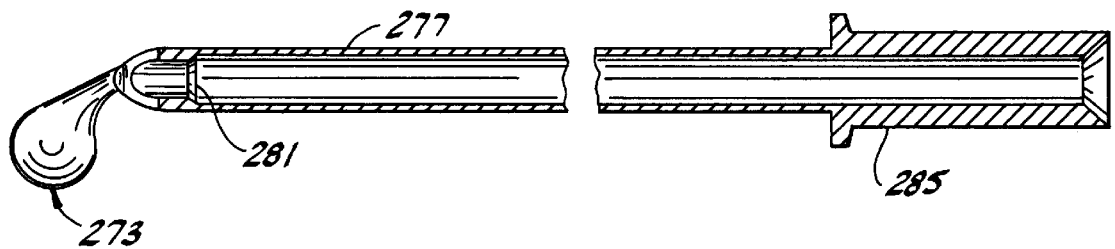

The system used to effect bovine embryo transplant is similar in certain respects to the system described above. It includes a probe, generally designated 271 in FIGS. 28–31, and the carrier 201 described above comprising straw 203, connector 217 and guide member 211. The probe 271 is very similar to probe 41 in that it comprises a slender, finger-like probing member 273 which curves forward and laterally outward from the probe body 277 in spiral fashion. However, in contrast to the probe 41 for pigs, the bovine probe 271 arches or spirals in the opposite direction as viewed from the front of the probe looking rearwardly (FIG. 29). This is to accommodate the physical anatomy of the bovine genital tract, which is different from a porcine tract. The probing member 273 has an enlarged ball-shaped tip 275 which is connected to the body 277 of the probe by a connecting arch 279. Like the probing member used in the probe 41 for pigs, the diameter of the probing member 273 for use in bovine is preferably 0.05–0.15 in. The diameter of the ball-shaped tip 275 of the probing member 273 may be 0.1–0.3 in. Additionally, the length of the arch 279 is preferably 0.4–1.0 in., the radii R1 and R2 (FIGS. 29 and 30) may be about 0.3 in., and the laterally outward projection of the probing member from the central longitudinal axis of the probe body may be 0.2–0.45 in. The probe body 277 has an internal shoulder 281 forming an abutment similar to the shoulder abutment 55 described above. This shoulder 281 is engageable by the annular stop 233 on the connector 217 of the carrier 201 during the transfer process. The probe body 277 has a handle 285 at its rearward end similar to handle 27, the rearward end of the passage through the probe being chamfered as indicated at 287 (FIG. 30) to facilitate insertion of the carrier into the probe. The overall length of the probe body 277 from its forward end to its rearward end may range from 14 in. to 20 in., which is generally shorter than the porcine probe body 43.

The system also includes an assisting bar similar to the testing bar 61 described previously.

Figure 32:
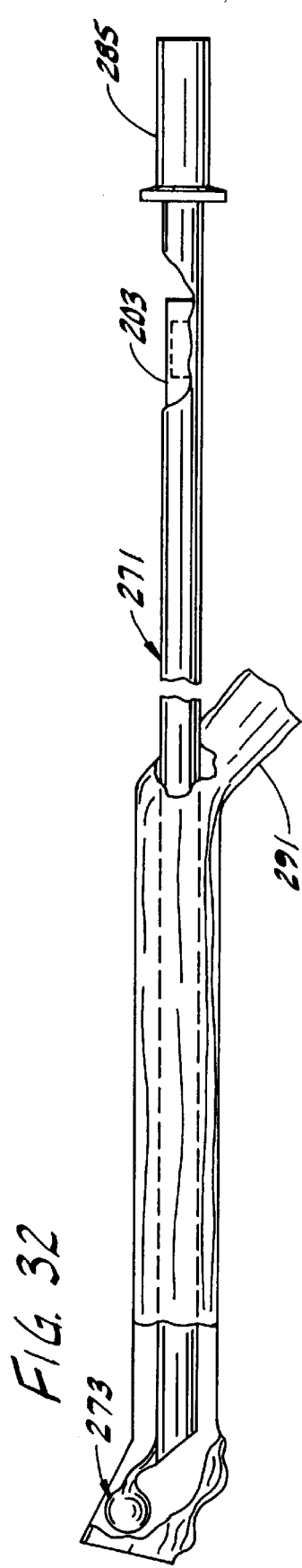
FIG. 32 is a view of an assembly of the carrier of FIG. 22 and the probe of FIG. 28.
Figure 33:
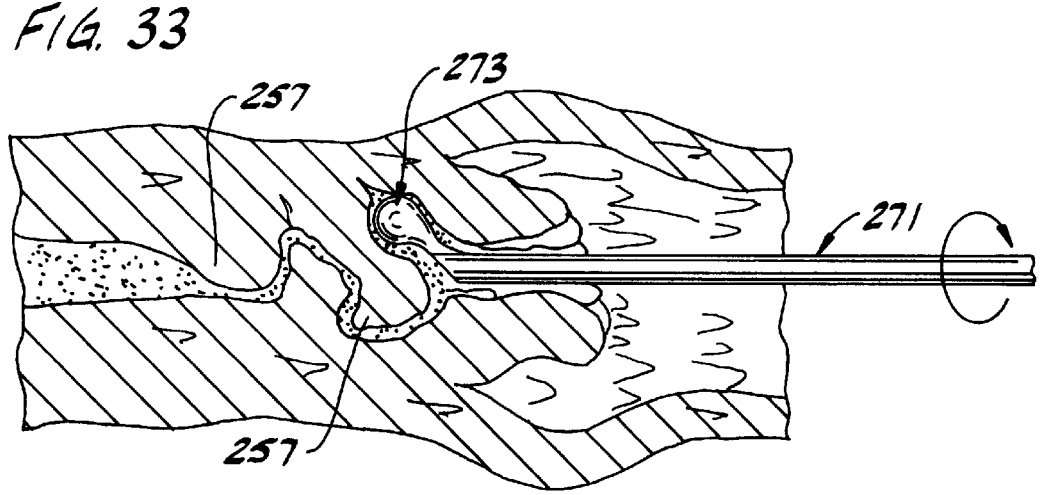
FIGS. 33–35 are views illustrating a bovine embryo transplant method using the assembly of FIG. 32.

To use this system for embryo transplant, embryos are loaded into the carrier 201 in the manner described above and shown in FIGS. 25 and 26. The carrier is then inserted into the rearward end of the probe 271 and the assembly is covered by a protective cover 291 (see FIG. 32.) Before insertion of the probe, a cow to receive the non-surgical transplant may be given a spinal epidural. The probe (with the carrier inside) is inserted forward end first into and through the vagina, following which the cover 291 is pulled back (and thus punctured) to expose the probing member 273. A hand can be inserted into the rectum of the animal to find the uterine horn 261 that is suitable for receiving an embryo transplant. This is done by determining which ovary has corpus luteum indicative of recent ovulation. After this has been accomplished, one hand should be used to hold the cervix 253 via the rectum, and the other hand should be used to manipulate the probe 271 through the cervical canal. This is accomplished by gently pushing the probe in a forward direction while simultaneously rotating it on its longitudinal axis in a clockwise direction, as indicated in FIG. 33. This procedure gently maneuvers the probing member 273 through plicae circulare 257 obstructing the cervical canal. (The curved, spiral configuration of the probing member causes it to thread through the cervical canal, like a screw, when the probe is rotated.) The enlarged tip 275 of the probing member minimizes the risk of damage to the genital tract. Excessive force should never be used. With the unique probe design of the present invention, if the cervical formations trap the probing member 273, a counterclockwise ¾ turn with slight pushing followed by clockwise turning and pushing will most likely free the probing member.

Figure 34:
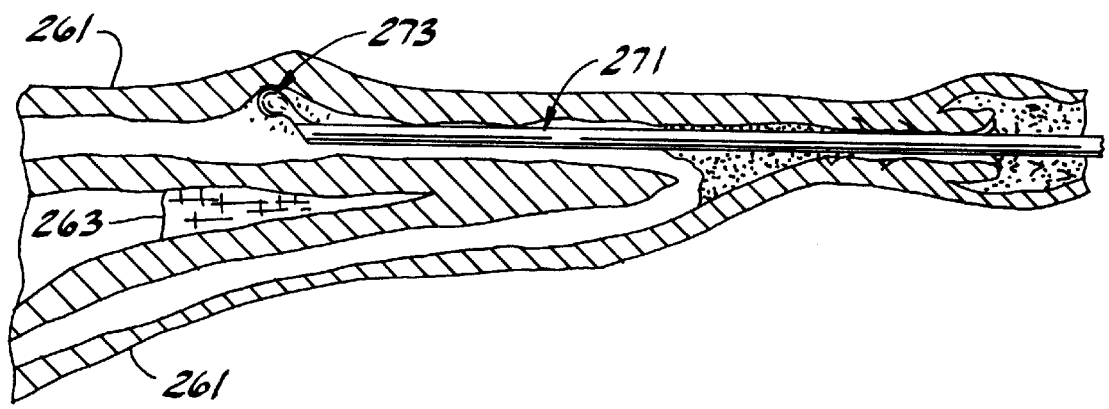
Figure 35:
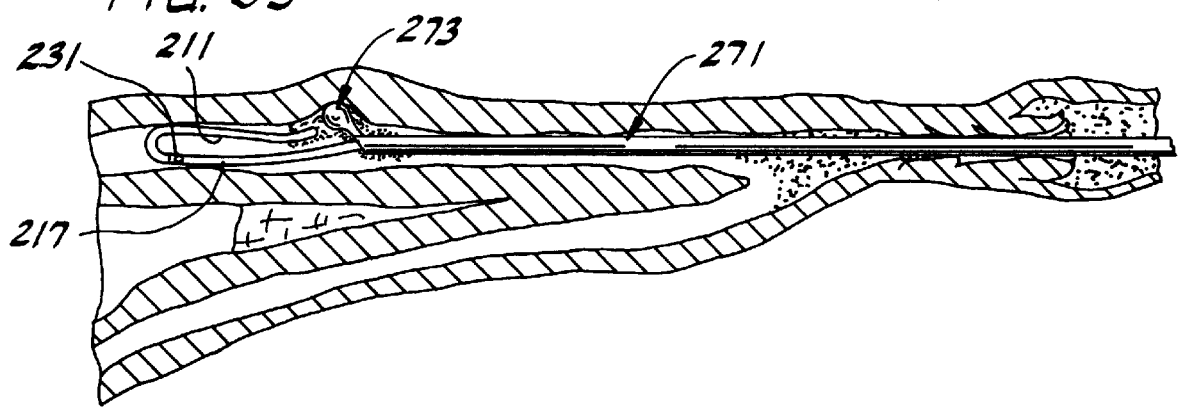
Figure 39:
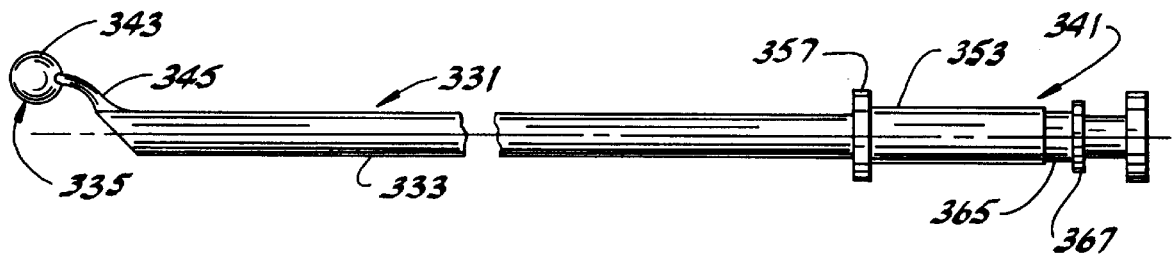
FIG. 39 is a side elevation of a modified probe of this invention equipped with gripping means for use with the carrier shown in FIG. 37.

After passing the cervix, the probing member 273 reaches the body 259 of the uterus, at which point the probing member should be forwarded deep into the appropriate uterine horn 261, as shown in FIG. 34, until the probing member passes the edge of the dorsal intercornual ligament 263. The assisting bar 61 is then inserted, wide end first, into the rearward end of the probe 271 to push the embryo carrier 201 forward to a fluid release position in which the flexible guide member 211 forms a loop in the uterine lumen. It may be helpful to use the hand in the rectum to guide the loop extension. If difficulties are encountered when forming the loop, the probe 271 may be pulled rearwardly while keeping the loop in fixed position until the stop 233 on the connector 217 of the embryo carrier engages the internal shoulder 281 adjacent the forward open end of the probe. This loop extension technique minimizes the risk of damage to the vulnerable and highly proliferated lumenal membrane. The semi-hard connector 217 to the rear of the guide member will bend but not loop, thus ensuring that the embryo release apertures 231 in the connector are properly positioned for a safe embryo deposition (see FIG. 35). The extension of the tubing loop also reduces the chances of mucus contamination and the risk embryos will be trapped in mucus collected on the probing member.

After the carrier 201 is in its fluid release position, the assisting bar 61 is inserted, narrow end first, into the rearward end of the probe 271 and moved forward until it engages the plug 209 in the rear end of the straw 203. Continued pushing of the assisting bar in a forward direction will move the plug forward in the straw to force the fluid out the open forward end of the straw and into the connector 217 for exit of the fluid and the embryos therein through the outlet apertures 231 in the connector for deposition in the uterine horn 261. After the embryos have been released, the assisting bar should be pulled rearwardly out of the probe. This will cause the tongues 67 on the assisting bar 61 to bite into the straw 203 and pull the carrier 201 out of the probe as well. The probe 271 should then be removed slowly from the animal.

Figure 36:
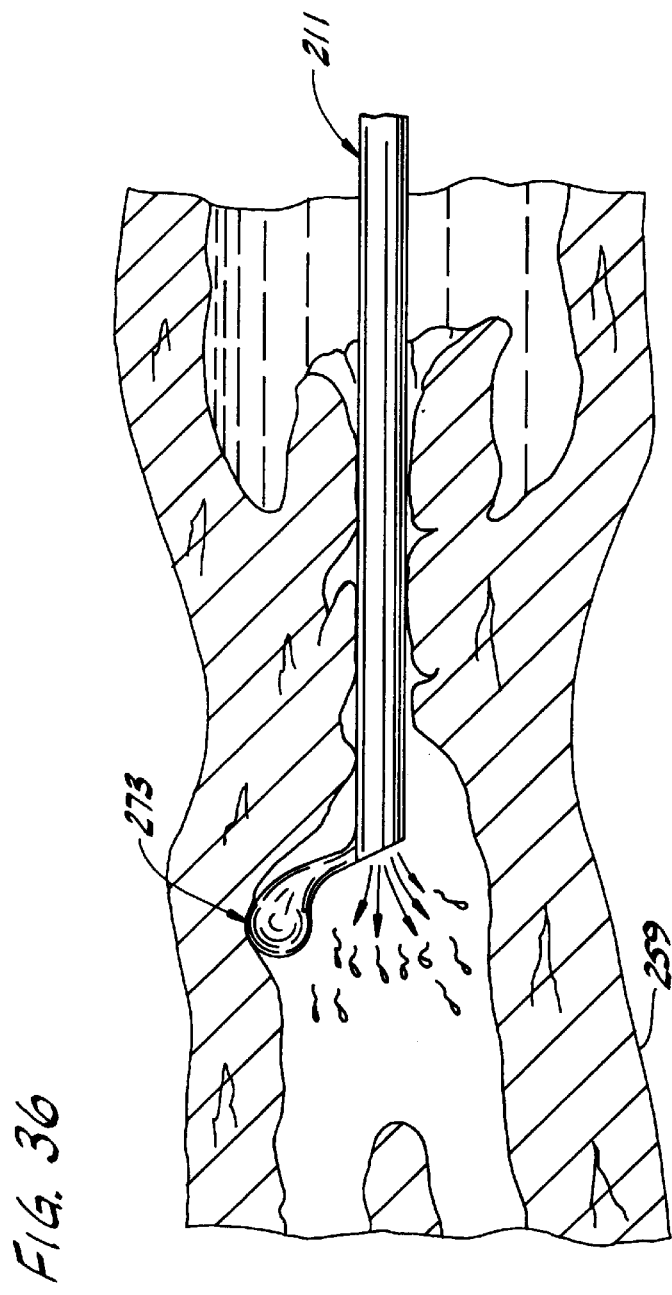
FIG. 36 is a view illustrating bovine artificial insemination using the straw component of FIG. 22A and the probe of FIG. 28.

The system described above can also be used for bovine AI. The procedure used for AI is much the same as described above except that semen is aspirated into the straw 203 of the carrier 201. The guide member 211 and connector 217 are not used in this procedure. The straw 203 containing the fluid is inserted into the probe 271 until the forward end of the straw engages the internal shoulder 281 of the probe. To accomplish AI, the probe is inserted into the animal, which may or may not be given a spinal epidural, until it reaches the body of the uterus, following which the assisting bar 61 is inserted, narrow end first, into the probe and moved forward into the straw to force semen out the forward end 207 of the straw and through the open forward end of the probe 271 into the uterus body 259, as depicted in FIG. 36. The procedure is completed by removing the assisting bar and straw from the probe and then slowly removing the probe from the animal.

The unique probe 271 of this invention may also be used in an embryo transplant process using a conventional embryo carrier for bovine, sometimes referred to as a "transplantation gun", generally designated 301 in FIGS. 37 and 38. This type of carrier (e.g., made in France by IMV, L'aigle) comprises a cannula generally indicated at 303 having a closed forward end 305, an open rearward end 307, and an overall length (e.g., 21 in.) greater than that of the probe (e.g., 14 in.) The cannula comprises a long straight plastic tube 309 having an outer diameter of 0.14 in., for example, and a polished metal tip 311 inserted into the forward end of the tube to close it. The cannula 303 has a fluid release port 315 adjacent its forward end 305 defined by a passage 317 in the tip communicating with the interior of the tube 309, and a pair of outlet openings 319 extending radially outwardly in opposite directions from the passage. A carrier 301 of this conventional type also includes a tubular fluid holder or "straw" 321 open at both ends and sized for insertion in the cannula 303 at its rearward end 307. This holder 321 is adapted to be loaded with a fluid medium containing embryos, as will be understood by those knowledgeable in this field. The straw has an absorbent expandable plug 323 in it (similar to plug 97 described above) which automatically seals the rearward end of the straw when a suitable amount of fluid has been aspirated into the straw through its open forward end.

FIGS. 39–42 illustrate a probe, generally designated 331, modified for use with a conventional carrier 301 of the type described above. The probe 331 is similar to the bovine probe 271 previously described, having a probe body 333, a probing member 335 at the forward end of the body curving forwardly and laterally outwardly in spiral fashion beyond the forward end of the probe body 333, and a passage 337 through the body through which the carrier may be inserted. However, this probe 331 is different in that it includes a gripping mechanism, generally indicated at 341, for gripping the cannula 303 and releasably holding it in selected axial positions relative to the probe so that the embryo transfer process to be described later can be conveniently carried out. The dimensions of the probe should also be suitable to handle the cannula. By way of example, the probing member 335 may have a diameter of 0.05–0.15 in., while the ball-shaped tip 343 of the probing member may have a diameter of 0.1–0.3 in.; the arch connector 345 may have a length of 0.4–1.0 in. with a bend radius of 0.3 in. (R1, R2), and may project laterally outward from the central longitudinal axis of the probe body 0.2–0.65 in.; and the probe body 333 may be formed from 6½ gage stainless steel tubing having an inside diameter of 0.168 in., an outside diameter of 0.188 in. (7-gage tubing can also be used having an inside diameter of 0.15 in and an outside diameter of 0.18 in.), and a length of 14–20 in.

Figure 40:
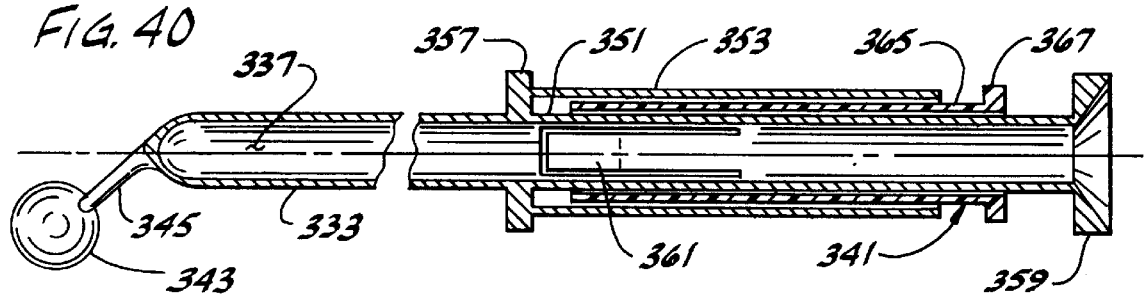
FIG. 40 is a cross sectional view of the probe and the aforementioned gripping mechanism.
Figure 41:
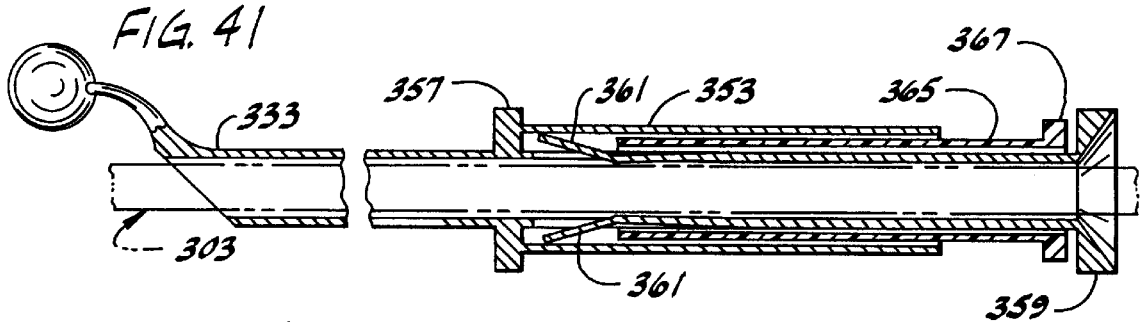
FIG. 41 is a view similar to FIG. 40 with the probe rotated 180 degrees on the axis of the probe and the gripping mecahanism rotated 90 degrees on the axis of the probe to show the gripping mechanism in a non-gripping position.
Figure 42:
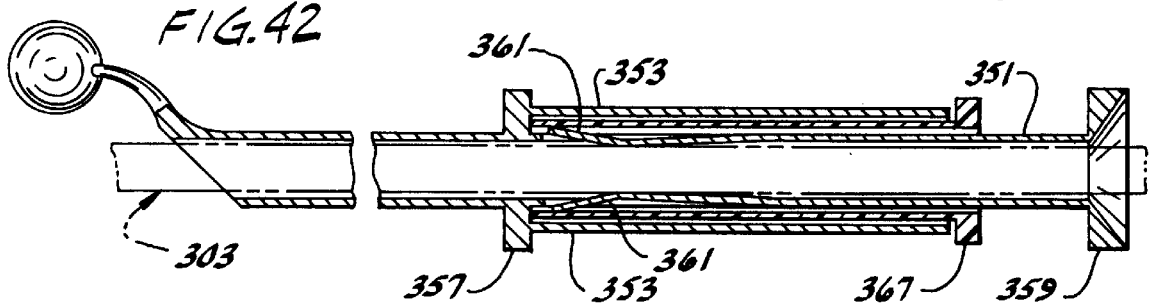
FIG. 42 is a view similar to FIG. 41 showing the gripping mechanism in a gripping position.

Referring to FIG. 40, the gripping mechanism 341 comprises inner and outer cylindric walls 351, 353 adjacent the rearward end of the probe 331. The walls 351, 353 are concentrically disposed with respect to one another and with respect to the central longitudinal axis of the probe. The outer wall 353 forms a handle having a length (e.g., 1.7 in.) sufficient for conveniently gripping the probe, and its outer surface may be roughened to enhance the grip. Both walls extend rearwardly from a radial flange 357 on the probe body 333. The inner wall 351 extends rearwardly beyond the outer wall 353 and has a peripheral flange 359 at its rearward end. The cylindric walls are formed from a resilient material, such as stainless steel tubing. The inner wall 351 is cut and bent as shown in FIG. 40 to form at least one and preferably two or more grippers in the form of cantilever gripping fingers 361, the free end portion of each gripping finger being resiliently movable radially inwardly and outwardly relative to the central axis of the probe from a non-gripping position (FIG. 41) to a gripping position (FIG. 42) in which the fingers are engageable with a cannula 303 in the probe for gripping and releasably holding it in selected axial positions relative to the probe. The resiliency of the material out of which the gripping fingers are made biases the fingers toward the non-gripping position of FIG. 41. It will be understood that the number and shape of the fingers 361 may vary without departing from the scope of this invention.

The gripping mechanism 341 also includes an actuator 365 in the form of a sleeve disposed between the inner and outer walls 351, 353 of the probe. The actuator 365 is manually movable axially relative to the central longitudinal axis of the probe between a release position (shown in FIG. 41) in which the gripping fingers 361 assume their relaxed, non-gripping position, and an actuating position (FIG. 42) in which the sleeve forces the resilient fingers inwardly against their natural bias to their gripping position. The rearward end of the sleeve 365 is formed with a flange 367 for assisting in moving the actuator between its actuating and release positions.

Figure 43:
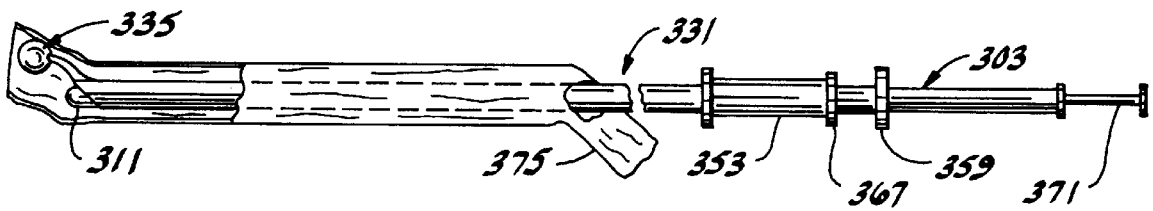
FIG. 43 is a view showing the carrier of FIG. 37 assembled with the probe of FIG. 39.

As mentioned, the modified probe 331 facilitates an embryo transplantation process using a carrier 301 of the type comprising cannula 303 and fluid holder 321. The first step of this process is to load a quantity of fluid containing embryos into the fluid holder 321, which may be a conventional embryo carrier straw, and then to insert the holder (straw) into the cannula 303 by a means of a pusher bar to a position in which the forward open end of the holder 321 is adjacent the forward end 305 of the cannula 303. An embryo release bar or ram 371 (FIG. 37) is then inserted into the rearward end 307 of the cannula, following which the cannula is inserted, forward end first, into the rearward end of the probe 331 and moved forward to a position in which the tip 311 of the cannula 303 protrudes slightly (e.g., 0.1 in.) through the forward open end of the probe body 333 (see FIG. 43.) The actuator sleeve 365 is slidably moved in a first forward direction to cause the gripping fingers 361 to move inwardly to grip the cannula 303 and hold it in this position in which the tip 311 of the cannula effectively blocks the opening into the probe body 333 to reduce the chances of bacterial contamination and contamination by mucus during the transplantation process. Also, the polished tip 311 of the cannula presents a smooth surface for passing through the genital tract of the animal, thereby reducing the risk of injury. After the cannula 303 has been inserted into the probe 331 and locked in position, the entire probe assembly is placed in a plastic cover 375 (FIG. 43) to reduce the risk of vaginal bacterial contamination.

Figure 44:
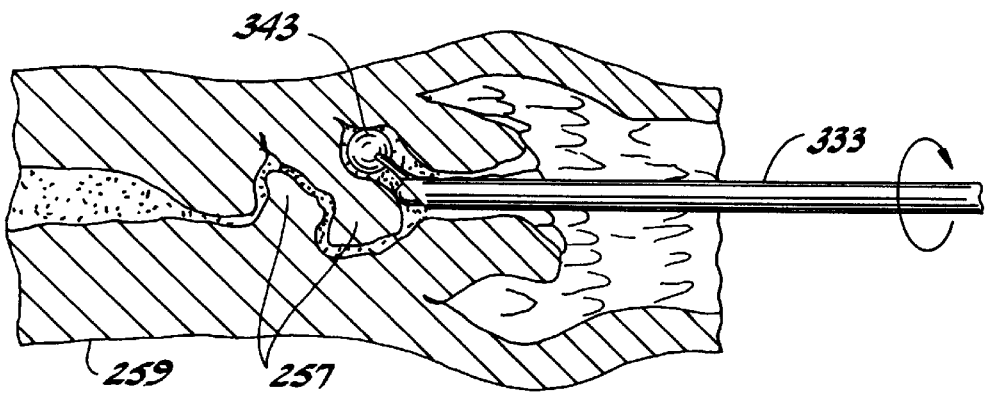
FIGS. 44–46 are views illustrating a bovine embryo transplant method using the assembly of FIG. 43.

Before insertion of the probe 331, a cow to receive the non-surgical embryo transplant may be given a spinal epidural. The probe 331 (with the carrier 301 inside) is then inserted, forward end first, into and through the vagina, following which the cover 375 is pulled back (and thus punctured) to expose the probing member 335. A hand can be inserted into the rectum of the animal to locate the uterine horn 261 that is suitable for receiving an embryo transplant. This is done by determining which ovary has corpus luteum indicative of recent ovulation. After this has been accomplished, one hand should be used to hold the cervix via the rectum, and the other hand is used to manipulate the probe through the cervical canal. This is accomplished by gently pushing the probe 331 in a forward direction while simultaneously rotating it on its longitudinal axis in a clockwise direction, as indicated in FIG. 44. This procedure gently maneuvers the probing member 335 through the plicae circulare 257 obstructing the cervical canal. The enlarged tip 343 of the probing member minimizes the risk of damage to the genital tract. Excessive force should never be used. With the unique probe design of the present invention, if the cervical formations trap the probing member 335, a counterclockwise ¾ turn with slight pushing followed by clockwise turning and pushing will most likely free the probing member.

Figure 45:
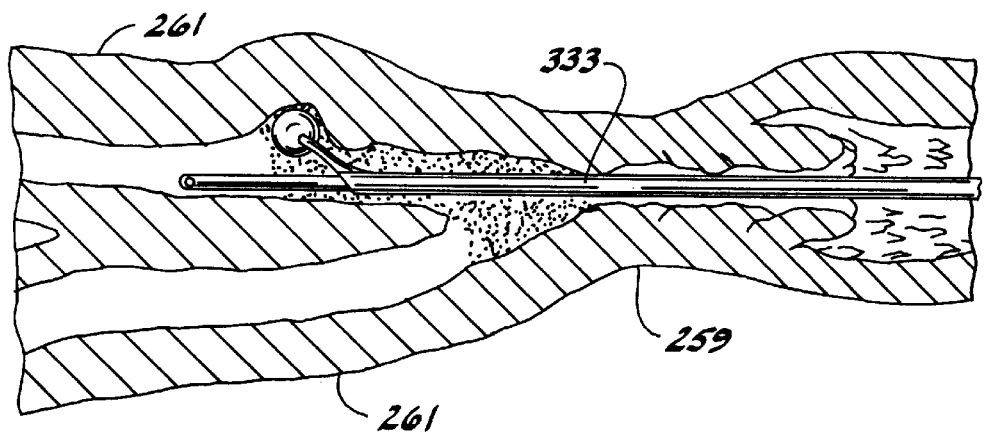

After passing the cervix, the probing member 335 reaches the body of the uterus, at which point the probing member is forwarded approximately 1 in. into the appropriate uterine horn, as shown in FIG. 45. At this point, the body 333 of the probe should be gripped with one hand through the rectum and uterine wall, and the other hand should be used to slide the actuator sleeve 365 on the probe in a rearward direction to enable the fingers 361 on the gripping mechanism 341 resiliently to move outwardly away from the cannula 303 to release it. The cannula, the rearward end of which projects rearwardly from the probe, can then be moved forward relative to the probe until its forward end is 2–3 in. deep in uterine horn, using the hand in the rectum to guide and assist such movement (FIG. 45.) During this movement, the tip of the cannula holds the mucus in place and thus prevents contamination mucus from being carried along with the cannula. The chances of mucus contamination can be further reduced by pulling the probing member back into the cervix while holding the cannula in place with the hand in the rectum.

Figure 46:
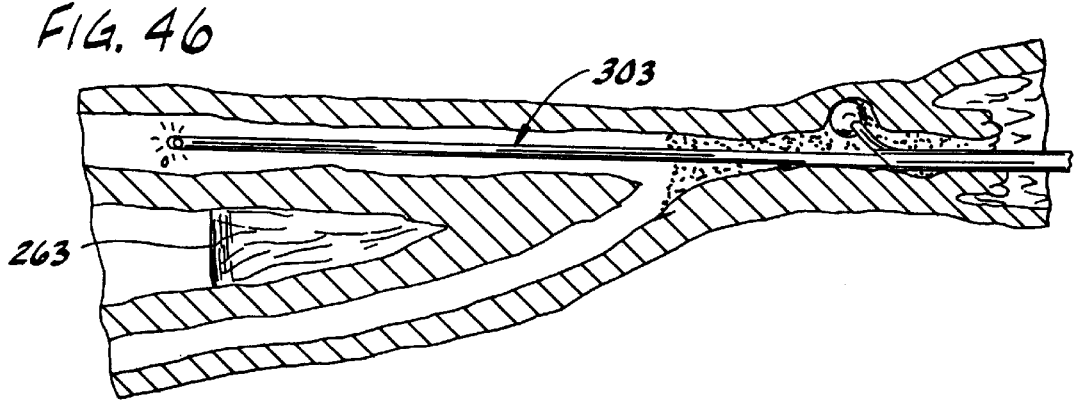

The cannula 303 is forwarded through the uterine horn until it passes the edge of the dorsal intercornual ligament 263, as shown in FIG. 46. The embryos-containing fluid is then released by using the ram 371 (which is sized for insertion into the holder 321) to push the plug 323 in the embryo holder forwardly to force the fluid out the open forward end of the holder and into the cannula for exit through the outlet openings 319 in the tip 311 of the cannula for deposit in the uterus. After the embryos are released, the cannula 303 is pulled rearwardly slowly and carefully back into the probe and the entire assembly is then pulled out of the genital tract.

It is contemplated that the present invention may be applicable to animals other than pigs and cows. For example, it is believed the system and methodology described above is suitable for transferring embryos to any female animal having a cervix structure which poses a natural barrier against the conveyance of embryos therethrough. It will also be understood that the probe of this system may be used in other non-surgical procedures which require penetration into the uterus of an animal, such as recovering fluid or tissue from the uterus of the animal.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense. claims

What is claimed is:

1. A system for introducing a fluid comprising either semen or a fluid medium containing embryos into the uterus of an animal, said uterus having a cervix leading to a uterus body, said system comprising a probe having a long tubular body with a central longitudinal axis, open forward and rearward ends, and a probing member curving forwardly and laterally outwardly beyond the forward end of the body, said probe being configured for insertion of the probing member and probe body, forward end first, inside the cervix of said animal and for manipulation of the probing member and probe body to gently maneuver the probing member in a forward direction through the cervix to a position in which the probing member and the forward open end of the probe body are adjacent the body of the uterus, and a fluid carrier for carrying fluid to be placed in the uterus of the animal, said fluid carrier being sized for insertion in and forward movement trough the probe body to a fluid release position for release of the fluid into the uterus.

2. A system as set forth in claim 1 wherein said fluid carrier comprises a cannula having a closed forward end, a rearward end, an overall length greater than that of the probe, and a fluid release port adjacent the forward end of the cannula, said cannula being sized in cross-section for insertion into and sliding movement within said probe, said fluid carrier further comprising a fluid holder having a fluid outlet, said holder being sized for insertion in said cannula and being adapted for release of fluid through the outlet of the holder into the cannula for exit through said fluid release port.

3. A system as set forth in claim 2 further comprising a ram sized for insertion through the rearward end of said cannula, said ram being manually pushable in a forward direction through said cannula to force fluid out of the fluid holder and into the fluid cannula for release into the uterus via said fluid release port.

4. A system as set forth in claim 2 further comprising a gripping mechanism for gripping said cannula and releasably holding the cannula in selected axial positions relative to the probe.

5. A system as set forth in claim 4 wherein said gripping mechanism comprises a gripping device on the probe movable between a non-gripping position and a gripping position in which the gripping device is engageable with said cannula to grip the cannula, and an actuator manually movable between an actuating position for moving the gripping device to said gripping position and a release position for enabling said gripping device to move to its non-gripping position.

6. A system as set forth in claim 5 wherein said gripping device comprises at least one gripping finger movable generally radially inwardly and outwardly relative to a central longitudinal axis of the probe between said gripping and non-gripping positions, and wherein said actuator comprises a sleeve slidable axially relative to said central longitudinal axis over said at least one gripping finger, said sleeve being slidable in a first direction for causing said at least one gripping finger to move to said gripping position and in a second direction for enabling said at least one gripping finger to move to said non-gripping position.

7. A system as set forth in claim 1 wherein said fluid carrier comprises a tubular straw having an open rearward end for connection to an aspirator, the straw further having an open forward end for aspiration of fluid into the straw, the fluid carrier further comprising a long flexible guide member for guiding the carrier into a fluid release position in the uterus, and a tubular connector for connecting the guide member to the open front end of the straw, said tubular connector having an outlet port in fluid communication with the open forward end of the straw for release of fluid in the straw through said outlet port.

8. A system as set forth in claim 7 further comprising an internal stop in the tubular body of the probe, and an external abutment on the tubular connector of the carrier engageable with said internal abutment on the probe body for limiting forward movement of the carrier relative to the probe body, said abutment and stop being so located that when they are in engagement the outlet port of the connector and said guide member are disposed forwardly beyond the forward open end of the probe body.

9. A method of effecting the non-surgical introduction of fluid comprising either semen or a fluid medium containing embryos into the uterus of an animal, said method involving the use of a probe having a long tubular body with a central longitudinal axis and an open forward end, and a probing member projecting in a generally non-axial direction from the probe body generally adjacent its forward end and extending outward beyond the forward end of the probe body, said method comprising the steps of inserting the probe, forward end first, into a cervix of the uterus of the animal, pushing the probe in a forward direction while simultaneously rotating the probe body about the central longitudinal axis of the probe body to cause said probing member to gently maneuver through the cervix until the probe body is in a forward position in which the forward end of the probe body is in the uterus of the animal, placing a fluid carrier carrying fluid inside the probe body, and releasing fluid from tie carrier into the uterus when the probe body is in its said forward position.

10. A method as set forth in claim 9 wherein said carrier comprises a fluid holder having a fluid outlet, and a cannula having a closed forward end, a rearward end, an overall length greater than that of said probe, and a fluid release port adjacent the forward end of the cannula, said cannula being sized in cross-section for insertion into and sliding movement within said probe, said method further comprising inserting said fluid holder in said cannula, inserting the cannula into said probe body to an intermediate position in which the forward end of the cannula is adjacent the forward open end of the probe body and blocks the open forward end of the probe body, inserting the probe with said cannula and fluid holder therein into the cervix of the animal and moving the probe body to its said forward position, and then, while holding the probe generally stationary, moving the cannula further forward to a fluid release position in which said fluid release port is disposed beyond the forward end of the probe body, and releasing the fluid through the outlet of the holder into the cannula for exit through said fluid release port into the uterus.

11. A method as set forth in claim 10 further comprising holding the cannula stationary relative to the probe body in said intermediate position until said probe is in its said forward position.

* * * * *